US010465175B2

(12) United States Patent
Rhee et al.

(10) Patent No.: US 10,465,175 B2
(45) Date of Patent: Nov. 5, 2019

(54) RECOMBINANT MICROORGANISM INCLUDING GENETIC MODIFICATION THAT INCREASES PYRUVATE, PHOSPHATE DIKINASE ACTIVITY AND USE THEREOF

(71) Applicant: Samsung Electronics Co., Ltd, Suwon-si, Gyeonggi-do (KR)

(72) Inventors: Hongsoon Rhee, Suwon-si (KR); Jinkyu Kang, Hwaseong-si (KR); Jinhwan Park, Suwon-si (KR); Dongsik Yang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/794,926

(22) Filed: Oct. 26, 2017

(65) Prior Publication Data

US 2018/0112197 A1  Apr. 26, 2018

(30) Foreign Application Priority Data

Oct. 26, 2016 (KR) .................. 10-2016-0140178

(51) Int. Cl.
*C12N 9/12* (2006.01)
*C12P 19/04* (2006.01)
*C12N 9/04* (2006.01)
*C12N 1/20* (2006.01)

(52) U.S. Cl.
CPC ............. *C12N 9/1294* (2013.01); *C12N 1/20* (2013.01); *C12N 9/0006* (2013.01); *C12P 19/04* (2013.01); *C12Y 101/01047* (2013.01); *C12Y 207/09001* (2013.01)

(58) Field of Classification Search
CPC ...... C12N 9/1294; C12N 9/0006; C12N 1/20; C12P 19/04; C12Y 207/09001; C12Y 101/01047
See application file for complete search history.

(56) References Cited

U.S. PATENT DOCUMENTS

| 5,912,156 A * | 6/1999 | Ohta ................. C12N 15/8273 435/194 |
| 6,054,305 A | 4/2000 | Tatsumi et al. |
| 7,396,977 B2 | 7/2008 | Usami et al. |
| 7,968,646 B2 | 6/2011 | Laborie et al. |
| 8,304,215 B2 | 11/2012 | Kim et al. |
| 8,551,502 B2 | 10/2013 | Wan et al. |
| 8,658,399 B2 | 2/2014 | Kim et al. |
| 8,679,779 B2 | 3/2014 | Bayon et al. |
| 9,260,720 B2 | 2/2016 | Hibberd et al. |
| 2005/0037082 A1 | 2/2005 | Wan et al. |
| 2011/0262696 A1 | 10/2011 | Bayon et al. |
| 2013/0011385 A1 | 1/2013 | Li et al. |
| 2014/0080184 A1 | 3/2014 | Saxena et al. |
| 2014/0356921 A1 | 12/2014 | Deng et al. |

FOREIGN PATENT DOCUMENTS

| EP | 0955497 A1 | 11/1999 | |
| JP | 2003-339392 | * 12/2003 | ............. C12P 19/04 |
| KR | 10-2004-0047951 A | 6/2004 | |
| WO | WO 2010/031154 A2 | 3/2010 | |
| WO | WO 2010/097623 A1 | 9/2010 | |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Benziman et al., Pyruvate-phosphate dikinase and the control of gluconeogenesis in Acetobacter xylinum. The J. Biol. Chem., 1971, vol. 246(1): 57-61. (Year: 1971).*
Ross et al., Cellulose biosynthesis and function in bacteria. Microbiol. Rev., 1991, vol. 55(1): 35-58. (Year: 1991).*
Gu et al., "Enhanced tolerance to drought in transgenic rice plants overexpressing $C_4$ photosynthesis enzymes", *The Crop Journal*, 105-114 (2013).
Li et al., "Improvement of bacteriol cellulose production by manipulating the metabolic pathways in which ethanol and sodium citrate involved", *Applied Microbiology and Biotechnology*, 96 (6): 1479-1487 (2012).
Naritomi et al., "Effect of Ethanol on Bacteriol Cellulose Production from Fructose in Continuous Culture", *Journal of Fermentation and Bioengineering*, 85 (6): 598-603 (1998).
Benziman et al., "Characterization and Properties of the Pyruvate Phosphorylation System of *Acetobacter xylinum*", *Journal of Bacteriology*, 104(1): 211-218 (1970).
Benziman et al., "Pyruvate-Phosphate Dikinase and the Control of Gluconeogenesis in *Acetobacter xylinum*", *The Journal of Biological Chemistry*, 246 (1): 57-61 (1971).
Eisaki et al., "Pyruvate phosphate dikinase from a thermophilic actinomyces *Microbispora rosea* subsp. *aerata*: purification, characterization and molecular cloning of the gene", *Biochimica et Biophysica Acta*, 1431 (2): 363-373 (1999).

(Continued)

*Primary Examiner* — Ganapathirama Raghu
(74) *Attorney, Agent, or Firm* — Leydig, Voit & Mayer, Ltd.

(57) ABSTRACT

Provided are a recombinant microorganism including a genetic modification that increases a pyruvate, phosphate dikinase activity, a method of producing cellulose using the same, and a method of producing a microorganism having enhanced cellulose productivity.

14 Claims, 3 Drawing Sheets

Specification includes a Sequence Listing.

(56) References Cited

OTHER PUBLICATIONS

Ross et al., "Cellulose Biosynthesis and Function in Bacteria", *Microbiology Reviews*, 55(1): 35-58 (1991).
Shigematsu et al., "Cellulose Production from Glucose Using a Glucose Dehydrogenase Gene (gdh)-Deficient Mutant of *Gluconacetobacter xylinus* and Its Use for Bioconversion of Sweet Potato Pulp", *Journal of Bioscience and Bioengineering*, 99(4): 415-422 (2005).
European Patent Office, extended European Search Report in Application No. 17198259.8, dated Dec. 8, 2017, 9 pages.

* cited by examiner

RECOMBINANT MICROORGANISM INCLUDING GENETIC MODIFICATION THAT INCREASES PYRUVATE, PHOSPHATE DIKINASE ACTIVITY AND USE THEREOF

CROSS-REFERENCE TO RELATED APPLICATION

This application claims the benefit of Korean Patent Application No. 10-2016-0140178, filed on Oct. 26, 2016, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 58,516 Byte ASCII (Text) file named "730503_ST25.TXT," created on Oct. 26, 2017.

BACKGROUND

1. Field

The present disclosure relates to a recombinant microorganism including a genetic modification that increases a pyruvate, phosphate dikinase activity, a method of producing cellulose using the same, and a method of producing a microorganism having enhanced cellulose productivity.

2. Description of the Related Art

Cellulose produced by microorganisms in culture, also known as microbial cellulose, exists as a primary structure of β-1,4 glucan composed of glucose, which form a network structure of fibril bundles.

Microbial cellulose is 100 nm or less in width, and, unlike plant cellulose, is free of lignin or hemicellulose. Additionally, compared to plant cellulose, microbial cellulose has higher wettability, higher water absorption capacity, higher tensile strength, higher elasticity, and higher heat resistance. Due to these characteristics, microbial cellulose has been developed by application to a variety of fields, such as cosmetics, medical products, dietary fibers, audio speaker diaphragms, and functional films.

Therefore, there is a need to develop new microorganisms and methods to increase the production of microbial cellulose. This invention provides such microorganisms and methods.

SUMMARY

Provided is a recombinant microorganism comprising a genetic modification that increases pyruvate, phosphate dikinase (PPDK) activity.

Also provided is a method of producing cellulose, the method comprising culturing a recombinant microorganism comprising a genetic modification that increases PPDK activity; and separating cellulose from the culture.

Further provided is a method of producing a microorganism having enhanced cellulose productivity, the method comprising introducing into a microorganism a genetic modification that increases PPDK activity.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
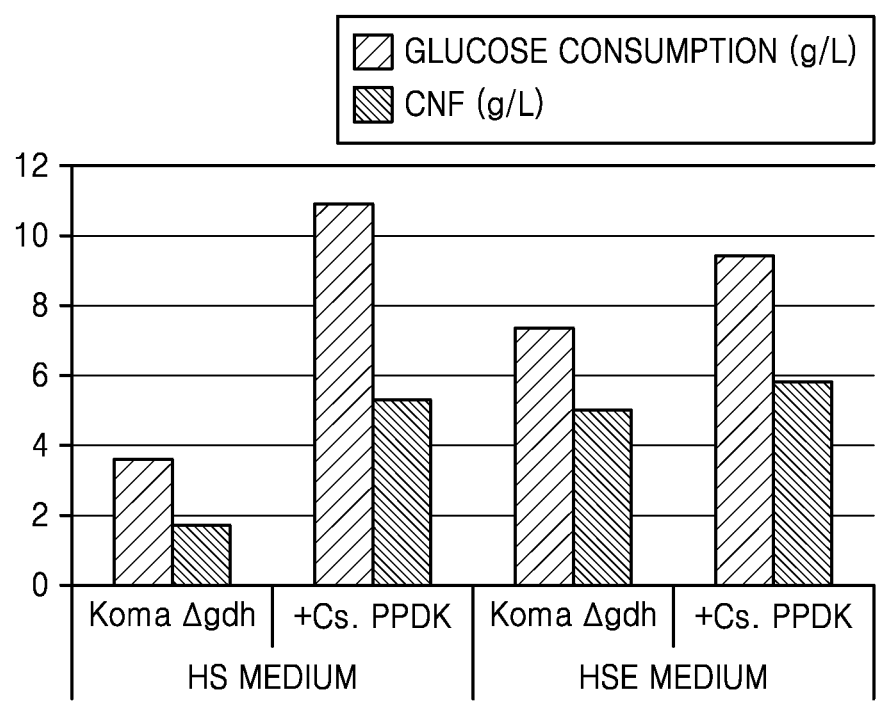
FIG. 1 is a graph of experimental data showing the cellulose nanofiber (CNF) production and glucose consumption of a PPDK gene-introduced *K. xylinus* strain (+Cs. PPDK) or a control *K. xylinus* (Koma Δgdh) strain under shaking culture.

The term "increase in activity" or "increased activity" or like terms, as used herein, refers to a detectable increase in the activity level of a modified (e.g., genetically engineered) cell, protein, or enzyme relative to the activity of a cell, protein, or enzyme of the same type, that does not have a given genetic modification (e.g., a parent cell or a native, original, or "wild-type" cell, protein, or enzyme). For example, an activity of a modified or engineered cell, protein, or enzyme may be increased by about 5% or more, about 10% or more, about 15% or more, about 20% or more, about 30% or more, about 50% or more, about 60% or more, about 70% or more, or about 100% or more relative to the activity of a cell, protein, or enzyme of the same type (e.g., a wild-type cell, protein, or enzyme) that does not have a given modification or has not been engineered. A cell having an increased activity of a protein or an enzyme may be identified by using any method known in the art.

A cell having increased activity of an enzyme or a polypeptide may be achieved by an increase in the expression of the enzyme or polypeptide, such as by increasing the copy number of the enzyme or polypeptide or by modification of a regulatory region of the enzyme or polypeptide gene. The modification of a regulatory region may be modification of promoter, operator or a polyadenylation site. The increased activity may also be due to an increase in the specific activity of the enzyme or polypeptide.

The "increase in expression" may be achieved by introduction or amplification of the gene encoding the enzyme or polypeptide. The introduction may be a transient introduction in which the gene is not integrated into a genome, or an introduction that results in integration of the gene into the genome. The introduction may be performed, for example, by introducing a vector comprising a polynucleotide encoding the enzyme or polypeptide into the cell.

The polynucleotide encoding the enzyme or polypeptide may be operably linked to one or more regulatory sequences that allow expression thereof, for example, a promoter, an enhancer, or a polyadenylation site. The enzyme or polypeptide encoded by the polynucleotide may be endogenous or exogenous to the microorganism in which it is inserted. As used herein, an endogenous gene refers to a gene that exists prior to a given genetic manipulation, for instance, in the genetic material of the wild-type or native microorganism, while the term "heterologous" means "foreign" or "not native" to the species. An exogenous gene refers to a gene that is externally introduced into the microorganism, and may be homologous or heterologous with respect to a host cell into which the gene is introduced.

An increase in copy number of a gene refers to any increase in copy number. For instance, an increase in copy number may be caused by introduction of an exogenous gene or amplification of an endogenous gene, and includes the introduction of a heterologous gene that does not exist in a non-engineered cell. The introduction of the gene may be mediated by a vehicle such as a vector. The introduction may be a transient introduction in which the gene is not integrated into a genome, or an introduction that results in integration of the gene into the genome. The introduction may be performed, for example, by introducing a vector into the cell, the vector including a polynucleotide encoding a target polypeptide, and then, replicating the vector in the cell, or by integrating the polynucleotide into the genome.

The introduction of the gene may be performed via any known method known in the art, for example, transformation, transfection, or electroporation.

The term "vehicle" or "vector", as used herein, refers to a nucleic acid molecule that is able to deliver nucleic acids encoding enzymes or polypeptides linked thereto into a cell. The vector may include, for example, a plasmid expression vector, a viral expression vector, such as a replication-defective retrovirus, adenovirus, or adeno-associated virus.

The term "inactivated" or "decreased" activity, as used herein, refers to a cell that has an activity of an enzyme or a polypeptide that is lower than the same activity measured in a parent cell (e.g., a non-genetically engineered cell). Also, the "inactivated" or "decreased" activity means that an isolated enzyme or a polypeptide has an activity that is lower than the same activity of an original or a wild-type enzyme or polypeptide. For example, a modified (e.g., genetically engineered) cell or enzyme has enzymatic activity of converting a substrate to a product, which shows about 5% or more, about 10% or more, about 20% or more, about 30% or more, about 40% or more, about 50% or more, about 55% or more, about 60% or more, about 70% or more, about 75% or more, about 80% or more, about 85% or more, about 90% or more, about 95% or more, or about 100% decrease, compared to that of the same type of cell or enzyme that does not have the modification, i.e., a parent cell or a "wild-type" cell or enzyme. Decreased activity of an enzyme or a cell may be confirmed by any method known in the art. The inactivation or decrease includes situations in which the enzyme has no activity, the enzyme has decreased activity even though the enzyme is expressed, or the enzyme-encoding gene is not expressed or expressed at a low level, compared to a cell having a non-modified gene, i.e., a parent cell or a wild-type cell.

The activity of an enzyme may be inactivated or decreased by deletion or disruption of a gene encoding the enzyme. The terms "deletion" or "disruption" of a gene refers to mutation of part or all of the gene or part or all of a regulatory sequence of the gene, (e.g., a promoter or a terminator region), such that the gene is either not expressed, expressed at a reduced level, or the gene product (e.g., enzyme) is expressed with no activity or reduced activity, compared to the naturally occurring gene product. The mutation may include addition, substitution, insertion, deletion, or conversion of one or more nucleotides of the gene. The deletion or disruption of a gene may be achieved by genetic manipulation such as homologous recombination, directed mutagenesis, or molecular evolution. When a cell includes a plurality of the same genes, or two or more different paralogs of a gene, one or more of the genes may be removed or disrupted. For example, inactivation or disruption of the enzyme may be caused by homologous recombination or may be performed by transforming the cell with a vector including a part of sequence of the gene, culturing the cell so that the sequence may homogonously recombine with an endogenous gene of the cell to delete or disrupt the gene, and then selecting cells, in which homologous recombination occurred, using a selection marker.

The genetic modification used in the present disclosure may be performed by a molecular biological method known in the art.

The term "parent cell" refers to an original cell, for example, a non-genetically engineered cell of the same type as an engineered microorganism. With respect to a particular genetic modification, the "parent cell" may be a cell that lacks the particular genetic modification, but is identical in all other respects. Thus, the parent cell may be a cell that is used as a starting material to produce a genetically engineered microorganism having an increased activity of a given protein (e.g., a protein having a sequence identity of about 95% or higher with respect to pyruvate, phosphate dikinase protein). The same comparison is also applied to other genetic modifications.

The term "gene", as used herein, refers to a nucleotide fragment encoding a particular protein, and may include a regulatory sequence of a 5'-non coding sequence and/or a 3'-non coding sequence.

The term "sequence identity" of a polynucleotide or a polypeptide, as used herein, refers to a degree of identity between bases or amino acid residues of sequences obtained after the sequences are aligned so as to best match in certain comparable regions. The sequence identity is a value that is measured by comparing two sequences in certain comparable regions via optimal alignment of the two sequences, in which portions of the sequences in the certain comparable regions may be added or deleted compared to reference sequences. A percentage of sequence identity may be calculated by, for example, comparing two optimally aligned sequences in the entire comparable region, determining the number of locations in which the same amino acids or nucleic acids appear to obtain the number of matching locations, dividing the number of matching locations by the total number of locations in the comparable regions (that is, the size of a range), and multiplying a result of the division by 100 to obtain the percentage of the sequence identity. The percentage of the sequence identity may be determined using a known sequence comparison program, for example, BLASTN (NCBI), BLASTP (NCBI), CLC Main Workbench (CLC bio), MegAlign™ (DNASTAR Inc), etc. Unless otherwise specified, selection of parameters used for operating the program is as follows: Ktuple=2, Gap Penalty=4, and Gap length penalty=12.

Various levels of sequence identity may be used to identify various types of polypeptides or polynucleotides having the same or similar functions or activities. For example, the sequence identity may include a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100%.

The term "genetic modification", as used herein, refers to an artificial alteration in a constitution or structure of a genetic material of a cell.

In the present disclosure, % represents w/w %, unless otherwise mentioned.

An aspect of the disclosure provides a recombinant microorganism comprising a genetic modification that increases pyruvate, phosphate dikinase (PPDK) activity.

PPDK is an enzyme belonging to the family of transferases that catalyzes the following chemical reaction:

ATP+pyruvate+phosphate⇔AMP+phosphoenolpyruvate (PEP)+diphosphate

The PPDK may belong to EC 2.7.9.1. The PPDK may be exogenous or endogenous. The PPDK may be derived from bacteria. The PPDK may be derived from the genus *Clostridium, Komagataeibacter, Propionibacterium, Acetobacter, Agrobacterium,* or *Escherichia* microorganism. The PPDK may be derived from *Komagataeibacter xylinus, Propionibacterium freudenreichii, Acetobacter aceti,* or *Clostridium symbiosum*. The PPDK may be a polypeptide having a sequence identity of about 95% or more with respect to any one amino acid sequence of SEQ ID NOS: 1 to 4. A gene encoding the PPDK may have a sequence identity of about 95% or more with respect to any one nucleotide sequence of SEQ ID NOS: 5 to 8.

With regard to the above microorganism, the genetic modification may increase expression of the gene encoding the PPDK. The genetic modification may increase the copy number of PPDK gene. The genetic modification may increase the copy number of the gene encoding the polypeptide having a sequence identity of 95% or more with respect to any one amino acid sequence of SEQ ID NOS: 1 to 4. The gene may have a sequence identity of about 95% or more with respect to any one nucleotide sequence of SEQ ID NOS: 5 to 8. The genetic modification may introduce the gene encoding PPDK, for example, via a vehicle such as a vector. The gene encoding the PPDK may exist within or outside the chromosome. The introduced gene encoding the PPDK may be a plurality of copies, for example, 2 or more, 5 or more, 10 or more, 30 or more, 50 or more, 100 or more, or 1000 or more copies.

The microorganism may be a cell of the family Acetobacteraceae. The cell of the family Acetobacteraceae may be a cell of the genus *Komagataibacter* (also called "*Gluconacetobacter*"), the genus *Acetobacter*, the genus *Clostridium*, or the genus *Gluconobacter*. The host cell may be *Komagataibacter xylinus* (also called "*Gluconacetobacter xylinus*"). The microorganism may belong to a genus *Escherichia*, or the genus *Propionibacterium*. The cell belonging to the genus *Escherichia* may be *E. coli*. The cell belonging to the genus *Propionibacterium* may be *Propionibacterium freudenreichii*. The cells belonging to the genus *Acetobacter* and the genus *Clostridium* may be *Acetobacter aceti* and *Clostridium symbiosum*, respectively.

The microorganism may further include a genetic modification that decreases the activity of membrane-bound glucose dehydrogenase (GDH). The genetic modification may inactivate or disrupt the gene encoding GDH. The genetic modification may remove or disrupt the gene encoding a polypeptide having a sequence identity of about 95% or more with respect to an amino acid sequence of SEQ ID NO: 9. The GDH gene may have a nucleotide sequence of SEQ ID NO: 10.

Another aspect of the disclosure provides a composition used for producing cellulose, the composition comprising the recombinant microorganism comprising a genetic modification that increases the PPDK activity.

The recombinant microorganism of the composition may be any microorganism with a genetic modification that increases PPDK activity described herein.

Still another aspect of the disclosure provides a method of producing cellulose, the method comprising culturing the recombinant microorganism comprising the genetic modification that increases the PPDK activity in a medium; and separating cellulose from a culture.

The recombinant microorganism of the method may be any microorganism with a genetic modification that increases PPDK activity described herein.

The culturing may be performed in a medium containing a carbon source, for example, glucose. The medium used for culturing the microorganism may be any general medium suitable for host cell growth, such as a minimal or complex medium containing appropriate supplements. The suitable medium may be commercially available or prepared by a known preparation method.

The medium may be a medium that may satisfy the requirements of a particular microorganism depending on a selected product of culturing. The medium may be a medium including components selected from the group consisting of a carbon source, a nitrogen source, a salt, trace elements, and combinations thereof.

The culturing conditions may be appropriately controlled for the production of a selected product, for example, cellulose. The culturing may be performed under aerobic conditions for cell proliferation. The culturing may be performed by static culture without shaking. A density of the microorganism may be a density which gives enough space so as not to disturb secretion of cellulose.

The term "culture conditions", as used herein, mean conditions for culturing the microorganism. Such culture conditions may include, for example, a carbon source, a nitrogen source, or an oxygen condition utilized by the microorganism. The carbon source that may be utilized by the microorganism may include monosaccharides, disaccharides, or polysaccharides. The carbon source may include glucose, fructose, mannose, or galactose as an assimilable glucose. The nitrogen source may be an organic nitrogen compound or an inorganic nitrogen compound. The nitrogen source may be exemplified by amino acids, amides, amines, nitrates, or ammonium salts. An oxygen condition for culturing the microorganism may be an aerobic condition of a normal oxygen partial pressure, a low-oxygen condition including about 0.1% to about 10% of oxygen in the atmosphere, or an anaerobic condition free of oxygen. A metabolic pathway may be modified in accordance with a carbon source or a nitrogen source that may be actually used by a microorganism. By this culturing, cellulose may be produced in a culture.

The culturing may be performed in a medium containing $Mg^{2+}$ ions of 1 mM to 15 mM. A concentration of the $Mg^{2+}$ ions may be 1 mM to 14 mM, 1 mM to 12 mM, 1 mM to 11 mM, 2 mM to 10 mM, 3 mM to 15 mM, 4 mM to 15 mM, 5 mM to 15 mM, 5 mM to 10 mM, 6 mM to 14 mM, 7 mM to 13 mM, 8 mM to 12 mM, 9 mM to 11 mM, or 9.5 mM to 10.5 mM. The culturing may be performed in a medium containing ethanol of 0.1 to 5% (v/v), for example, 0.1 to 3% (v/v), 0.5 to 2.5% (v/v), 0.5 to 2% (v/v), 0.5 to 1.5% (v/v), 0.5 to 1.0% (v/v), 0.7 to 3.0% (v/v), 0.7 to 2.5% (v/v), 0.7 to 1.0% (v/v), or 1.0% to 2.0% (v/v). The medium may be an Hestrin-Schramm (HS) or HS plus ethanol (HSE) medium. The $Mg^{2+}$ may be also included in the form of a salt in the medium. The salt may be, for example, $SO_4^{2-}$ salt.

The method may include separating the cellulose from the culture. The separating may be, for example, collecting of a cellulose pellicle formed on the top of the medium. The cellulose pellicle may be collected by physically stripping off the cellulose pellicle or by removing the medium. The separating may be collecting of the cellulose pellicle while maintaining its shape without damage. Further, the cellulose may be suspended in the medium or may have a pellet shape. The separating the cellulose may be performed by a centrifugation, precipitation, or filtration process. Further, the separating may be appropriately controlled depending on static culture or shaking culture.

Still another aspect provides a method of producing a microorganism having enhanced cellulose productivity, the method comprises introducing into a microorganism a genetic modification that increases the PPDK activity. The gene encoding PPDK may be introduced into the microorganism by a vehicle comprising the gene. The method may further include introducing a genetic modification that decreases an activity of membrane-bound glucose dehydrogenase. The microorganism may belong to the family Acetobacteraceae.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items.

Hereinafter, the present invention will be described in more detail with reference to Examples. However, these Examples are provided for illustrative purposes only, and the invention is not intended to be limited by these Examples.

Example 1. Preparation of *K. xylinus* Including Pyruvate, Phosphate Dikinase (PPDK) Gene and Production of Cellulose In this Example, *Komagataeibacter xylinus* (Korean Culture Center of Microorganisms, KCCM 41431) and GDH gene-deleted *K. xylinus* were introduced with an exogenous PPDK gene, and the microorganisms introduced with the gene were cultured to produce cellulose, thereby examining effects of the gene introduction on cellulose productivity. Here, the term "exogenous" gene also includes a native gene that exists endogenously, but is introduced from outside. The PPDK gene was derived from *Komagataeibacter xylinus*, *Propionibacterium freudenreichii*, *Acetobacter aceti*, and *Clostridium symbiosum*.

(1) Preparation of GDH Gene-Deleted *K. xylinus*

The membrane-bound pyrroloquinoline-quinone (PQQ)-dependent glucose dehydrogenase (GDH) gene in *K. xylinus* was inactivated by homologous recombination. A specific procedure is as follows.

To delete GDH gene by homologous recombination, fragments of the 5'- and 3'-ends of GDH gene were obtained by PCR amplification using a genomic sequence of *K. xylinus* as a template and a set of primers of GDH-5-F(SEQ ID NO: 11) and GHD-5-R(SEQ ID NO: 12) and a set of primers of GDH-3-F(SEQ ID NO: 13) and GHD-3-R(SEQ ID NO: 14). Further, a neo gene (nptll) fragment which is a kanamycin resistance gene derived from Tn5 was obtained by PCR amplification using a set of primers of SEQ ID NO: 15 and SEQ ID NO: 16. Three of the fragments of the 5'- and 3'-ends of GDH gene and the kanamycin resistance gene fragment were cloned into SacI and XbaI restriction sites of a pGEM-3zf vector (#P2271, Promega Corp.) using an In-fusion HD cloning kit (#PT5162-1, Clontech) to prepare pGz-dGDH. This vector thus obtained was transformed into *K. xylinus* by electroporation. The transformed *K. xylinus* strain was spread on an HS-agar medium (0.5% peptone, 0.5% yeast extract, 0.27% $Na_2HPO_4$, 0.15% citric acid, 2% glucose, and 1.5% bacto-agar) supplemented with 100 μg/ml of kanamycin, and then cultured at 30° C. A strain having a kanamycin resistance was selected to delete GDH gene. As a result, GDH gene deletion was confirmed, and this strain was designated as *K. xylinus* (Δgdh).

(2) Introduction of PPDK Gene

Each of PPDK genes derived from *Komagataeibacter xylinus*, *Propionibacterium freudenreichii*, *Acetobacter aceti*, and *Clostridium symbiosum*, that is, nucleotide sequences of SEQ ID NOS: 5 to 8 was introduced into *K. xylinus* and *K. xylinus* (Δgdh), respectively. A specific introduction procedure is as follows.

PPDK gene derived from the microorganism *Komagataeibacter xylinus* was obtained by PCR using a primer set of SEQ ID NOS: 17 and 18 as primers and a genomic sequence of *Komagataeibacter xylinus* as a template. PPDK gene derived from the microorganism *Propionibacterium freudenreichii* was obtained by PCR using a primer set of SEQ ID NOS: 19 and 20 as primers and a genomic sequence of *Propionibacterium freudenreichii* as a template. PPDK gene derived from the microorganism *Acetobacter acet* was obtained by PCR using a primer set of SEQ ID NOS: 21 and 22 as primers and a genomic sequence of *Acetobacter aceti* as a template. Codons of a PPDK nucleotide sequence derived from *Clostridium symbiosum* were optimized to *Komagataeibacter xylinus*, and synthesized. PPDK gene derived from the microorganism *Clostridium symbiosum* was obtained by PCR using a primer set of SEQ ID NOS: 23 and 24 as primers and the codon-optimized *Clostridium symbiosum* PPDK nucleotide sequence as a template.

Each gene was cloned into the PstI restriction site of a pCSa vector (SEQ ID NO: 25) using an In-fusion HD cloning kit (#PT5162-1, Clontech) to allow expression under Tac promoter. Each vector thus obtained was transformed into *K. xylinus* by electroporation. The transformed *K. xylinus* strain was spread on an HS-agar medium (0.5% peptone, 0.5% yeast extract, 0.27% $Na_2HPO_4$, 0.15% citric acid, 2% glucose, and 1.5% bacto-agar) supplemented with 100 μg/ml of chloramphenicol, and then cultured at 30° C. Strains having a chloramphenicol resistance were selected to prepare PPDK gene-overexpressing strains.

(3) Glucose Consumption and Cellulose Production

The designated *K. xylinus* strains were inoculated into a 125-mL flask containing 25 ml of HS medium (0.5% peptone, 0.5% yeast extract, 0.27% $Na_2HPO_4$, 0.15% citric acid, and 2% glucose) or HSE medium, respectively and cultured at 230 rpm at 30° C. for 5 days. The HSE medium was the same as the HS medium, except that HSE medium further included 1(v/v) % ethanol. Then, glucose consumption and the product cellulose were quantified. During culturing of the PPDK gene-overexpressing recombinant strains, 100 μg/ml of chloramphenicol was added to media. After culturing, a culture was filtered to remove cells, and the culture was subjected to high performance liquid chromatography (HPLC) equipped with an Aminex HPX-87H column (Bio-Rad, USA) to analyze glucose. cellulose production was measured after washing cellulose solids formed in the flask with 0.1 N sodium hydroxide and water, drying the cellulose solids in an oven at 60° C., and then weighing.

FIG. 1 shows cellulose nanofiber (CNF) production and glucose consumption of PPDK gene-introduced *K. xylinus* (Δgdh) strain under shaking culture. As shown in FIG. 1, in the HS medium, the PPDK gene-introduced *K. xylinus* (Δgdh) (experimental group) showed about 2.9-fold increase in glucose consumption from 3.6 g/L to 10.31 g/L, and about 3.1-fold increase in CNF production from 1.7 g/L to 5.2 g/L, compared to K. xylinus(Δgdh) (control group). In the HSE medium, the experimental strain showed about 1.3-fold increase in glucose consumption and about 1.2-fold increase in CNF production, compared to the control group. In FIG. 1, Koma Δgdh represents K. xylinus(Δgdh) and +Cs PPDK represents PPDK-introduced K. xylinus(Δgdh).

Table 1 shows cellulose nanofiber (CNF) productions and glucose consumptions of PPDK gene-introduced K. xylinus (Δgdh) strains under shaking culture in the HS medium. In Table 1, KomaΔgdh represents control K. xylinus(Δgdh), and Kx. PPDK, Pf.PPDK, Aa.PPDK and Cs.PPDK represent strains prepared by introducing the control strain with the PPDK genes derived from Komagataeibacter xylinus, Propionibacterium freudenreichii, Acetobacter aceti, and Clostridium symbiosum, respectively.

TABLE 1

|  | Glucose consumption (g/L) | CNF (g/L) |
| --- | --- | --- |
| KomaΔgdh | 2.9 | 1.4 |
| Kx.PPDK | 4.5 | 2.1 |
| Pf.PPDK | 5.8 | 3.1 |
| Aa.PPDK | 3.6 | 2.6 |
| Cs.PPDK | 10.31 | 5.2 |

(4) Effect of Pyrophosphate Concentration

The effect of varying concentrations of pyrophosphate (PPi) on glucose consumption and CNF production was measured in K. xylinus(Δgdh) (control group) and PPDK gene-introduced K. xylinus(Δgdh) (Cs.PPDK experimental group).

Culturing was performed in the same manner as in section (3), except that a predetermined concentration of sodium pyrophosphate was added to HS media.

As a result, when 5 mM PPi was added to the control group, inhibitions of glucose consumption and cellulose synthesis were observed. However, in the experimental strain, no inhibition of glucose consumption was observed, and glucose consumption was improved even at a concentration of 5 mM.

Figure 2:
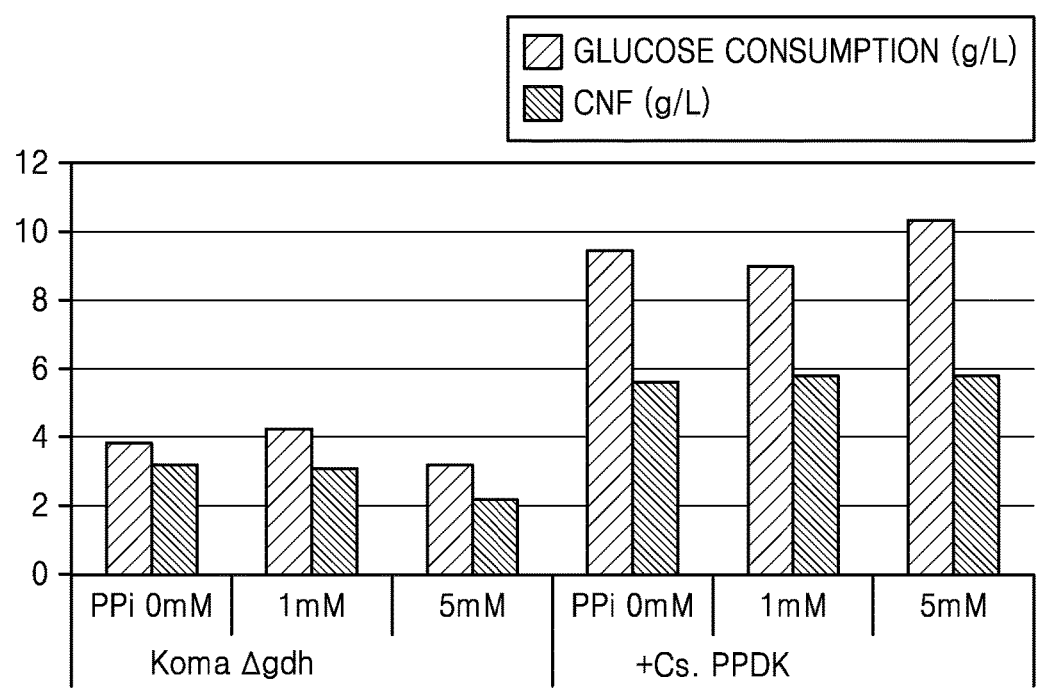
FIG. 2 is a graph of experimental data showing the glucose consumption and CNF production in *K. xylinus* (Koma Δgdh) (control group) and PPDK gene-introduced *K. xylinus* (+Cs. PPDK) (experimental group) cultured in increasing concentrations of pyrophosphate (PPi)

FIG. 2 shows glucose consumptions and CNF productions of K. xylinus(Δgdh) (control group) and PPDK gene-introduced K. xylinus(Δgdh) (experimental group) according to a concentration of pyrophosphate (PPi).

(5) Effect of $Mg^{2+}$ Ion Concentration

The effect of varying concentrations of $Mg^{2+}$ ions on glucose consumption and CNF production was measured in K. xylinus(Δgdh) (control group) and PPDK gene-introduced K. xylinus(Δgdh) (experimental group).

Culturing was performed in the same manner as in section (3), except that a predetermined concentration of $Mg^{2+}$ ions was added in the form of $MgSO_4$ to HS media.

Figure 3:
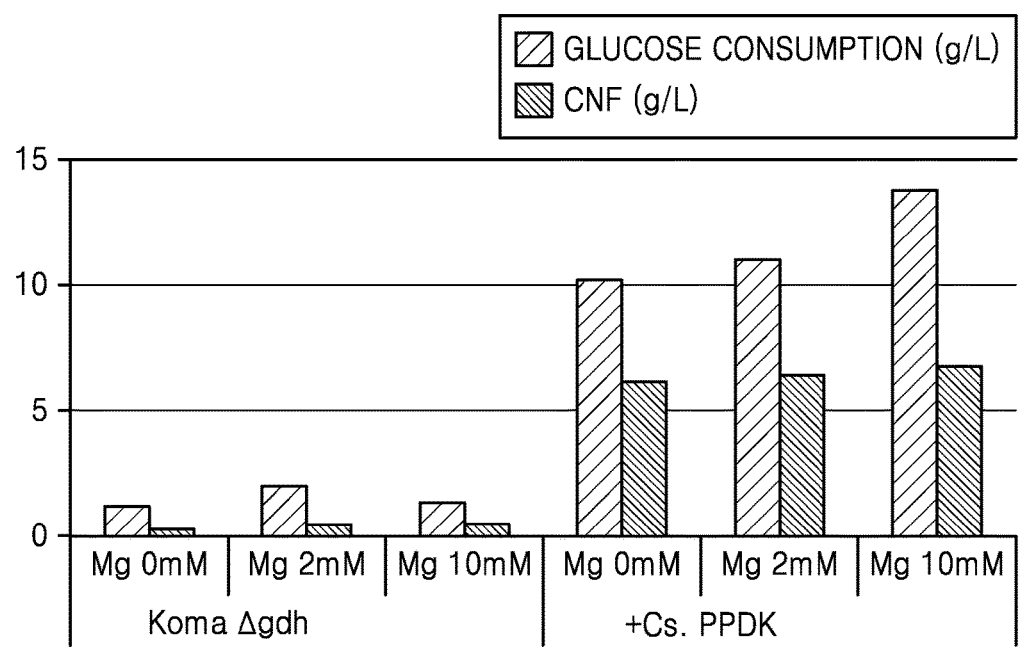
FIG. 3 is a graph of experimental data showing the glucose consumption and CNF production in *K. xylinus* (Koma Δgdh) (control group) and PPDK gene-introduced *K. xylinus*(+Cs. PPDK) (experimental group) cultured in increasing concentrations of $Mg^{2+}$ ions.

FIG. 3 shows glucose consumption and CNF production according to a concentration of $Mg^{2+}$ ion. As shown in FIG. 3, glucose consumption and cellulose production were increased with increasing concentration of $Mg^{2+}$ ions. Table 2 shows the results of FIG. 3.

TABLE 2

|  | Glucose consumption (g/L) | | | CNF production (g/L) | | |
| --- | --- | --- | --- | --- | --- | --- |
| Mg Conc. (mM) | 0 | 2 | 10 | 0 | 2 | 10 |
| Koma Δgdh | 1.2 | 2.0 | 1.3 | 0.28 | 0.42 | 0.48 |
| +Cs PPDK | 10.31 | 11.1 | 13.9 | 6.16 | 6.46 | 6.78 |

Further, a weight average molecular weight (DPw) and a volume average molecular weight (DPv) of cellulose thus produced was measured.

The degree of polymerization (DP) of CNF was measured as a degree of polymerization determined by viscosity measurement (DPv) and a weight average degree of polymerization (DPw).

For measurement of DPw, 5 mg of a freeze-dried CNF sample was derivatized with addition of 10 mL of pyridine and 1 mL of phenyl isocyanate at 100° C. for 48 hours. Derivatized CNF was added to 2 mL of methanol, and 100 mL of 70% methanol was further added to solidify the derivatized CNF, followed by washing with water twice. Water was removed from CNF thus prepared under vacuum, and then 1 ml of tetrahydrofuran per 1 mg of CNF was used, followed by incubation at 50° C. for 1 hour. A molecular weight, a molecular weight distribution, and a length distribution of CNF were determined by gel permeation chromatography (GPC). GPC experiment was performed on Waters Alliance e2695 separation module (Milford, Mass., USA) equipped with Waters 2414 refractive index detector and Styragel HR2, HR4, HMW7 column. Tetrahydrofuran was used as an eluent at a flow rate of 0.5 mL/min. The CNF incubated in tetrahydrofuran was filtered using a 0.15 um syringe filter (PTFE), and then injected (injection volume: 20 uL). Polystyrene (PS, #140) standards were used to calibrate a curve.

15 mg of freeze-dried CNF was incubated in 15 mL of a 0.5 M cupriethylenediamine solution for about 2 hours, and its viscosity was examined by a visco pump (ACS370) and a viscometer (Ubbelohde).

TABLE 3

|  | DPv | | DPw | |
| --- | --- | --- | --- | --- |
| Mg Conc. (mM) | 0 | 10 | 0 | 10 |
| Koma | 3884 | No experiment | 8331 | No experiment |
| Koma Δgdh | 3880 | 4434 | 8321 | 9516 |
| +Cs PPDK | 3941 | 4751 | 8408 | 10199 |

As shown in Table 3, effects of improving the polymerization degree by addition of magnesium ions were observed in the control strain and the experimental strain, and the effects of improving the polymerization degree in the control strain and the experimental strain were 14% and 21%, respectively. The effect in the PPDK gene-introduced experimental strain was higher than that in the control strain.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant microorganism comprising
a genetic modification that increases pyruvate, phosphate dikinase (PPDK) enzyme activity as compared with a microorganism without the genetic modification, wherein the PDDK enzyme belongs to EC 2.7.9.1,
and a genetic modification that decreases membrane-bound glucose dehydrogenase (GDH) activity as compared with a microorganism not comprising the genetic modification;
wherein the microorganism is *Clostridium, Komagataeibacter, Propionibacterium, Acetobacter, Agrobacterium,* or *Escherichia*.

2. The recombinant microorganism of claim 1, wherein the genetic modification that increases PDDK activity is a genetic modification that increases the copy number of a gene encoding the PPDK.

3. The recombinant microorganism of claim 2, wherein the PPDK gene is from *Clostridium, Komagataeibacter, Propionibacterium, Acetobacter, Agrobacterium,* or *Escherichia*.

4. The recombinant microorganism of claim 1, wherein PPDK is a polypeptide having 95% or higher sequence identity to any of SEQ ID NOs: 1 to 4.

5. The recombinant microorganism of claim 2, wherein the PPDK gene has 95% or higher sequence identity to any of SEQ ID NOs: 5 to 8.

6. The recombinant microorganism of claim 1, wherein the genetic modification that decreases membrane-bound glucose dehydrogenase activity is a genetic modification that inactivates or disrupts a gene encoding the membrane-bound glucose dehydrogenase.

7. A method of producing cellulose, the method comprising culturing a recombinant microorganism of claim 1 in a medium; and separating cellulose from the culture.

8. The method of claim 7, wherein the genetic modification increases the copy number of a gene encoding the PPDK.

9. The method of claim 7, wherein the medium comprises 1 to 15 mM Mg'.

10. The method of claim 7, wherein the PPDK is a polypeptide having 95% or higher sequence identity to SEQ ID NO: 1.

11. The method of claim 8, wherein the PPDK gene has 95% or higher sequence identity to SEQ ID NO: 2.

12. The recombinant microorganism of claim 1, wherein the genetic modification that increases PPDK activity is a copy number increase in an exogenous gene encoding the PPDK.

13. The recombinant microorganism of claim 1, wherein the genetic modification that increases PPDK activity is a copy number increase in a heterologous gene encoding the PPDK.

14. The recombinant microorganism of claim 1, wherein the recombinant microorganism comprises a heterologous gene encoding PDDK, and a genetic modification that inactivates or disrupts a gene encoding the membrane-bound glucose dehydrogenase.

* * * * *

SEQUENCE LISTING

<160> NUMBER OF SEQ ID NOS: 25

<210> SEQ ID NO 1
<211> LENGTH: 891
<212> TYPE: PRT
<213> ORGANISM: Komagataeibacter xylinum

<400> SEQUENCE: 1

Met Thr Lys Trp Val Tyr Ser Phe Gly Asp Gly Leu Asn Glu Gly Arg
1               5                   10                  15

Ala Glu Met Arg Asn Leu Leu Gly Gly Lys Gly Ala Asn Leu Ala Glu
            20                  25                  30

Met Ala Ala Asn Gly Leu Pro Val Pro Pro Gly Phe Thr Ile Thr Thr
        35                  40                  45

Glu Val Cys Ser Ala Phe Tyr Glu Asn Gly Arg Lys Tyr Pro Asp Asp
    50                  55                  60

Leu Arg Ala Gln Val Ala Asp Ala Leu Ala Arg Val Glu Lys Ser Met
65                  70                  75                  80

Gly Leu Arg Phe Gly Asp Ala Ala Pro Leu Leu Val Ser Val Arg
                85                  90                  95

Ser Gly Ala Arg Val Phe Met Pro Gly Met Met Asp Thr Val Leu Asn
            100                 105                 110

Leu Gly Leu Asn Asp Glu Thr Val Glu Gly Leu Ala Arg Ser Ser Gly
        115                 120                 125

Asp Ala Arg Phe Ala Trp Asp Ser Tyr Arg Arg Phe Ile Gln Met Tyr
    130                 135                 140

Gly Ser Val Val Met Gly Val Pro His His Phe Glu Asp Val Leu
145                 150                 155                 160

Glu Gln Phe Lys Arg Ala Ser Lys Val Glu Asp Asp Thr Ala Ile Thr
                165                 170                 175

Ala Glu Gln Trp Arg Thr Ile Val Ala Asp Tyr Arg His Leu Ile Ser
            180                 185                 190

Thr His Ala Gly Thr Glu Phe Pro Thr Asp Pro Gln Asp Gln Leu Trp
        195                 200                 205

Gly Ala Ile Gly Ala Val Phe Gly Ser Trp Met Asn Pro Arg Ala Asn
    210                 215                 220

Thr Tyr Arg Arg Leu His Glu Ile Pro Ala Ser Trp Gly Thr Ala Val
225                 230                 235                 240

-continued

```
Asn Val Gln Ser Met Val Phe Gly Asn Met Gly Glu Asp Cys Ala Thr
                245                 250                 255
Gly Val Cys Phe Thr Arg Asp Pro Ser Thr Gly Glu Asn Ile Phe Tyr
            260                 265                 270
Gly Glu Tyr Leu Ile Asn Ala Gln Gly Glu Asp Val Val Ala Gly Ile
        275                 280                 285
Arg Thr Pro Gln Pro Met Ala Cys Ala Arg Ala Glu Ala Gly Gln His
    290                 295                 300
Pro Met Glu Thr Thr Leu Pro Gln Ala Tyr Ala Glu Leu Met Arg Val
305                 310                 315                 320
Arg Ser Val Leu Glu Thr His Tyr Lys Asp Met Gln Asp Ile Glu Phe
                325                 330                 335
Thr Val Gln Arg Asn Val Leu Tyr Ile Leu Gln Thr Arg Ser Gly Lys
            340                 345                 350
Arg Thr Ala Ala Ala Leu Lys Ile Ala Ile Asp Met Ala Arg Glu
        355                 360                 365
Gly Leu Ile Thr Gln Glu Asp Ala Ile Arg Arg Val Pro Ala Ser Ser
    370                 375                 380
Leu Asp Gln Leu Leu His Pro Thr Leu Asp Pro Lys Ala Glu Arg Val
385                 390                 395                 400
Gln Leu Thr Arg Gly Leu Pro Ala Ser Pro Gly Ala Ala Ala Gly Ala
                405                 410                 415
Val Val Phe Ser Ala Glu Glu Cys Glu Ala Arg Ala Lys Gly Glu
            420                 425                 430
Asp Val Ile Leu Val Arg Ile Glu Thr Ser Pro Glu Asp Val His Gly
        435                 440                 445
Met His Ala Ala Arg Gly Val Leu Thr Thr Arg Gly Gly Met Thr Ser
    450                 455                 460
His Ala Ala Val Val Ala Arg Gly Met Gly Arg Val Cys Val Ala Gly
465                 470                 475                 480
Ala Gly Ser Ile His Val Asp Tyr Ala Ala Gly Thr Met Thr Ile Gly
                485                 490                 495
Thr His Thr Ile Ala Gln Gly Glu Trp Ile Thr Leu Asp Gly Gly Thr
            500                 505                 510
Gly Ala Val Tyr Leu Gly Arg Val Pro Thr Ile Ala Pro Thr Leu Ser
        515                 520                 525
Asp Asp Phe Asn Thr Leu Met Gly Trp Ala Asp Ser Val Arg Arg Leu
    530                 535                 540
Gly Val Arg Ala Asn Ala Glu Thr Pro Asp Asp Ala Ala Thr Ala Arg
545                 550                 555                 560
Arg Phe Gly Ala Glu Gly Ile Gly Leu Ala Arg Thr Glu His Met Phe
                565                 570                 575
Phe Gly Pro Asp Arg Ile Gly Leu Val Arg Gln Met Ile Ile Ala Asp
            580                 585                 590
Asp Glu Leu Val Arg Gln Lys Ala Ile Ala Gly Leu Leu Pro Phe Gln
        595                 600                 605
Arg Asp Asp Phe Ala Ser Leu Phe Arg Ile Met Ala Gly Leu Pro Val
    610                 615                 620
Thr Val Arg Leu Leu Asp Pro Pro Leu His Glu Phe Leu Pro His Ala
625                 630                 635                 640
Glu Ala Glu Met Val Glu Val Ala Gln Ala Leu Gly Lys Ser Val Glu
                645                 650                 655
```

```
Glu Val Arg Ala Arg Cys Ala Ala Leu Ala Glu Thr Asn Pro Met Leu
            660                 665                 670

Gly His Arg Gly Cys Arg Leu Gly Leu Thr Ser Pro Glu Ile Tyr Ala
        675                 680                 685

Met Gln Val Arg Ala Leu Ile Gln Ala Ala Val Ile Val Glu Lys Glu
    690                 695                 700

Leu Gly Lys Pro Ile Arg Pro Glu Ile Met Ile Pro Leu Val Ala Thr
705                 710                 715                 720

Gln Ala Glu Leu Ala Thr Thr Arg Arg Ala Glu Asp Glu Ile Ala
                725                 730                 735

Arg Val Leu Lys Glu Glu Gly Thr Asn Leu Asn Tyr Tyr Ile Gly Thr
                740                 745                 750

Met Ile Glu Leu Pro Arg Ala Ala Ile Gln Ala Asp Arg Ile Ala Glu
            755                 760                 765

Tyr Ala Asp Phe Phe Ser Phe Gly Thr Asn Asp Leu Thr Gln Thr Thr
        770                 775                 780

Phe Gly Leu Ser Arg Asp Asp Ala Gly Ser Phe Leu Pro Tyr Tyr Val
785                 790                 795                 800

Asp Asn Gly Leu Leu Pro Arg Asp Pro Phe Val Ser Ile Asp Arg Asp
                805                 810                 815

Gly Val Gly Ala Leu Val Arg Leu Gly Val Glu Arg Gly Arg Gln Thr
            820                 825                 830

Ser Pro Asp Leu Lys Leu Gly Ile Cys Gly Glu His Gly Asp Pro
                835                 840                 845

Asp Ser Ile Ala Phe Phe Glu Glu Val Gly Leu Asp Tyr Val Ser Cys
    850                 855                 860

Ser Pro Phe Arg Val Pro Val Ala Arg Leu Ala Ala Ala Gln Ala Ala
865                 870                 875                 880

Leu Ala Thr Arg Ser Lys Val Gly Asn Pro Ala
                885                 890

<210> SEQ ID NO 2
<211> LENGTH: 840
<212> TYPE: PRT
<213> ORGANISM: Propionibacterium freudenreichii

<400> SEQUENCE: 2

Met Ala Lys Trp Val Tyr Lys Phe Glu Glu Gly Asn Ala Ser Met Arg
1               5                   10                  15

Asn Leu Leu Gly Gly Lys Gly Cys Asn Leu Ala Glu Met Thr Ile Leu
                20                  25                  30

Gly Met Pro Ile Pro Gln Gly Phe Thr Val Thr Thr Glu Ala Cys Thr
            35                  40                  45

Glu Tyr Tyr Asn Ser Gly Lys Gln Ile Thr Gln Glu Ile Gln Asp Gln
        50                  55                  60

Ile Phe Glu Ala Ile Thr Trp Leu Glu Glu Leu Asn Gly Lys Lys Phe
65                  70                  75                  80

Gly Asp Thr Glu Asp Pro Leu Leu Val Ser Val Arg Ser Ala Ala Arg
                85                  90                  95

Ala Ser Met Pro Gly Met Met Asp Thr Ile Leu Asn Leu Gly Leu Asn
            100                 105                 110

Asp Val Ala Val Glu Gly Phe Ala Lys Lys Thr Gly Asn Pro Arg Phe
        115                 120                 125

Ala Tyr Asp Ser Tyr Arg Arg Phe Ile Gln Met Tyr Ser Asp Val Val
    130                 135                 140
```

-continued

```
Met Glu Val Pro Lys Ser His Phe Glu Lys Ile Ile Asp Ala Met Lys
145                 150                 155                 160

Glu Glu Lys Gly Val His Phe Asp Thr Asp Leu Thr Ala Asp Asp Leu
                165                 170                 175

Lys Glu Leu Ala Glu Lys Phe Lys Ala Val Tyr Lys Glu Ala Met Asn
            180                 185                 190

Gly Glu Glu Phe Pro Gln Glu Pro Lys Asp Gln Leu Met Gly Ala Val
        195                 200                 205

Lys Ala Val Phe Arg Ser Trp Asp Asn Pro Arg Ala Ile Val Tyr Arg
210                 215                 220

Arg Met Asn Asp Ile Pro Gly Asp Trp Gly Thr Ala Val Asn Val Gln
225                 230                 235                 240

Thr Met Val Phe Gly Asn Lys Gly Glu Thr Ser Gly Thr Gly Val Ala
                245                 250                 255

Phe Thr Arg Asn Pro Ser Thr Gly Glu Lys Gly Ile Tyr Gly Glu Tyr
            260                 265                 270

Leu Ile Asn Ala Gln Gly Glu Asp Val Val Ala Gly Val Arg Thr Pro
        275                 280                 285

Gln Pro Ile Thr Gln Leu Glu Asn Asp Met Pro Asp Cys Tyr Lys Gln
290                 295                 300

Phe Met Asp Leu Ala Met Lys Leu Glu Lys His Phe Arg Asp Met Gln
305                 310                 315                 320

Asp Met Glu Phe Thr Ile Glu Glu Gly Lys Leu Tyr Phe Leu Gln Thr
                325                 330                 335

Arg Asn Gly Lys Arg Thr Ala Pro Ala Ala Leu Gln Ile Ala Cys Asp
            340                 345                 350

Leu Val Asp Glu Gly Met Ile Thr Glu Glu Ala Val Val Arg Ile
        355                 360                 365

Glu Ala Lys Ser Leu Asp Gln Leu Leu His Pro Thr Phe Asn Pro Ala
370                 375                 380

Ala Leu Lys Ala Gly Glu Val Ile Gly Ser Ala Leu Pro Ala Ser Pro
385                 390                 395                 400

Gly Ala Ala Ala Gly Lys Val Tyr Phe Thr Ala Asp Glu Ala Lys Ala
                405                 410                 415

Ala His Glu Lys Gly Glu Arg Val Ile Leu Val Arg Leu Glu Thr Ser
            420                 425                 430

Pro Glu Asp Ile Glu Gly Met His Ala Ala Glu Gly Ile Leu Thr Val
        435                 440                 445

Arg Gly Gly Met Thr Ser His Ala Ala Val Val Ala Arg Gly Met Gly
450                 455                 460

Thr Cys Cys Val Ser Gly Cys Gly Glu Ile Lys Ile Asn Glu Glu Ala
465                 470                 475                 480

Lys Thr Phe Glu Leu Gly Gly His Thr Phe Ala Glu Gly Asp Tyr Ile
                485                 490                 495

Ser Leu Asp Gly Ser Thr Gly Lys Ile Tyr Lys Gly Asp Ile Glu Thr
            500                 505                 510

Gln Glu Arg Ser Val Ser Gly Ser Phe Glu Arg Ile Met Val Trp Ala
        515                 520                 525

Asp Lys Phe Arg Thr Leu Lys Val Arg Thr Asn Ala Asp Thr Pro Glu
530                 535                 540

Asp Thr Leu Asn Ala Val Lys Leu Gly Ala Glu Gly Ile Gly Leu Cys
545                 550                 555                 560
```

-continued

Arg Thr Glu His Met Phe Phe Glu Ala Asp Arg Ile Met Lys Ile Arg
            565                 570                 575

Lys Met Ile Leu Ser Asp Ser Val Glu Ala Arg Glu Glu Ala Leu Asn
            580                 585                 590

Glu Leu Ile Pro Phe Gln Lys Gly Asp Phe Lys Ala Met Tyr Lys Ala
            595                 600                 605

Leu Glu Gly Arg Pro Met Thr Val Arg Tyr Leu Asp Pro Pro Leu His
            610                 615                 620

Glu Phe Val Pro His Thr Glu Glu Gln Ala Glu Leu Ala Lys Asn
625                 630                 635                 640

Met Gly Leu Thr Leu Ala Glu Val Lys Ala Lys Val Asp Glu Leu His
            645                 650                 655

Glu Phe Asn Pro Met Met Gly His Arg Gly Cys Arg Leu Ala Val Thr
            660                 665                 670

Tyr Pro Glu Ile Ala Lys Met Gln Thr Arg Ala Val Met Glu Ala Ala
            675                 680                 685

Ile Glu Val Lys Glu Glu Thr Gly Ile Asp Ile Val Pro Glu Ile Met
            690                 695                 700

Ile Pro Leu Val Gly Glu Lys Lys Glu Leu Lys Phe Val Lys Asp Val
705                 710                 715                 720

Val Val Glu Val Ala Glu Gln Val Lys Lys Glu Lys Gly Ser Asp Met
            725                 730                 735

Gln Tyr His Ile Gly Thr Met Ile Glu Ile Pro Arg Ala Ala Leu Thr
            740                 745                 750

Ala Asp Ala Ile Ala Glu Glu Ala Glu Phe Phe Ser Phe Gly Thr Asn
            755                 760                 765

Asp Leu Thr Gln Met Thr Phe Gly Phe Ser Arg Asp Asp Ala Gly Lys
            770                 775                 780

Phe Leu Asp Ser Tyr Tyr Lys Ala Lys Ile Tyr Glu Ser Asp Pro Phe
785                 790                 795                 800

Ala Arg Leu Asp Gln Thr Gly Val Gly Gln Leu Val Glu Met Ala Val
            805                 810                 815

Lys Lys Gly Arg Gln Thr Arg Pro Gly Leu Lys Cys Gly Ile Cys Gly
            820                 825                 830

Glu His Gly Glu Ile Leu Leu Pro
            835                 840

<210> SEQ ID NO 3
<211> LENGTH: 890
<212> TYPE: PRT
<213> ORGANISM: Acetobacter aceti

<400> SEQUENCE: 3

Met Thr Lys Trp Val Tyr Ser Phe Gly Gly Gly Leu Asn Glu Gly Ser
1               5                   10                  15

Ala Gly Met Arg Asn Leu Leu Gly Gly Lys Gly Ala Asn Leu Ala Glu
            20                  25                  30

Met Ala Ser Ile Gly Leu Pro Val Pro Pro Gly Phe Thr Ile Thr Thr
            35                  40                  45

Glu Val Cys Ser Ala Tyr Tyr Asp Asn Gly Asn Ala Tyr Pro Ala Asp
            50                  55                  60

Leu Ala Glu Gln Val Ala Ala Leu His Arg Val Glu Lys Ser Val
65                  70                  75                  80

Gly Leu Val Phe Gly Asp Ala Thr Ala Pro Leu Leu Val Ser Val Arg
            85                  90                  95

-continued

```
Ser Gly Ala Arg Val Ser Met Pro Gly Met Met Asp Thr Val Leu Asn
            100                 105                 110

Leu Gly Leu Asn Asp Glu Thr Val Glu Gly Leu Ala Ala Ser Ser Lys
        115                 120                 125

Asp Glu Arg Phe Ala Trp Asp Ser Tyr Arg Arg Phe Ile Gln Met Tyr
    130                 135                 140

Gly Ser Val Val Met Gly Val Pro His His Arg Phe Glu Asp Leu Leu
145                 150                 155                 160

Glu Gln Ala Lys His Gly Leu Gly Val Thr Asp Asp Thr Ala Ile Lys
                165                 170                 175

Ala Ser Asp Trp Arg Glu Ile Val Lys Asp Tyr Lys Asp Ile Val Gln
            180                 185                 190

Lys Glu Thr Gly Lys Pro Phe Pro Asn Asp Pro Gln Glu Gln Leu Trp
        195                 200                 205

Gly Ala Ile Ser Ala Val Phe Gly Ser Trp Met Asn Pro Arg Ala His
    210                 215                 220

Thr Tyr Arg Lys Leu His Asp Ile Pro Ala Ser Trp Gly Thr Ala Val
225                 230                 235                 240

Asn Val Gln Ala Met Val Phe Gly Asn Met Gly Asp Asp Cys Ala Thr
                245                 250                 255

Gly Val Cys Phe Thr Arg Asp Pro Ser Thr Gly Glu Asn Ile Phe Tyr
            260                 265                 270

Gly Glu Tyr Leu Val Asn Ala Gln Gly Glu Asp Val Val Ala Gly Ile
        275                 280                 285

Arg Thr Pro Gln Pro Met Ser Ala Ala Arg Ala Ala Ala Asp Gln Ser
    290                 295                 300

Pro Met Glu Lys Val Leu Pro Glu Ala Tyr Lys Glu Leu Met Arg Val
305                 310                 315                 320

Arg Asp Ile Leu Glu Lys His Tyr Arg Asp Met Gln Asp Ile Glu Phe
                325                 330                 335

Thr Val Gln Ser Asn Val Leu Tyr Met Leu Gln Thr Arg Ser Gly Lys
            340                 345                 350

Arg Thr Ala Ala Ala Leu Lys Ile Ala Ile Asp Met Ala Gln Glu
        355                 360                 365

Gly Leu Ile Thr Gln Glu Glu Ala Ile Gln Arg Val Pro Pro Gly Ser
    370                 375                 380

Leu Asp Gln Leu Leu His Pro Thr Leu Asp Pro Lys Ala Glu Lys Asn
385                 390                 395                 400

Leu Phe Ser Arg Gly Leu Pro Ala Ser Pro Gly Ala Ala Ala Gly Ala
                405                 410                 415

Ile Val Phe Thr Ala Glu Glu Val Glu Asp Arg Ala Ala Lys Gly Glu
            420                 425                 430

Asp Val Ile Leu Val Arg Ile Glu Thr Ser Pro Glu Asp Val His Gly
        435                 440                 445

Met His Ala Ala Arg Gly Val Leu Thr Thr Arg Gly Gly Met Thr Ser
    450                 455                 460

His Ala Ala Val Val Ala Arg Gly Met Gly Arg Val Cys Val Ala Gly
465                 470                 475                 480

Ala Gly Gly Ile Thr Val Asp Tyr Lys Ala Gln Thr Met Thr Val Gly
                485                 490                 495

Asn Val Thr Leu Lys Gly Gly Asp Trp Ile Thr Leu Asp Gly Gly Thr
            500                 505                 510
```

Gly Ala Val Tyr Val Gly Lys Val Ala Thr Ile Pro Pro Thr Leu Ser
            515                 520                 525

Gly Asp Phe Ser Thr Leu Met Gly Trp Ala Asp Glu Val Arg Arg Leu
        530                 535                 540

Arg Val Arg Ala Asn Ala Glu Thr Pro Glu Asp Ala Glu Thr Ala Arg
545                 550                 555                 560

Arg Phe Gly Ala Glu Gly Ile Gly Leu Ser Arg Thr Glu His Met Phe
                565                 570                 575

Phe Gly Pro Asp Arg Ile Gly Phe Val Arg Gln Met Ile Met Ser Asp
            580                 585                 590

Asp Pro Ala Thr Arg Lys Lys Ala Ile Asp Ala Leu Leu Pro Phe Gln
        595                 600                 605

Arg Asp Asp Phe Ser Gln Ile Phe Arg Ile Met Ser Gly Leu Pro Val
610                 615                 620

Thr Ile Arg Leu Leu Asp Pro Pro Leu His Glu Phe Leu Pro His Gly
625                 630                 635                 640

Glu Thr Glu Leu Glu Val Ala Thr Ala Leu Gly Gln Ser Val Glu
                645                 650                 655

Ser Leu Arg Ala Arg Arg Ser Ala Leu Ser Glu Ala Asn Pro Met Leu
                660                 665                 670

Gly His Arg Gly Cys Arg Leu Gly Ile Thr Tyr Pro Glu Ile Tyr Ala
            675                 680                 685

Met Gln Val Arg Ala Ile Ile Glu Ala Ala Ile Ala Val Ser Lys Glu
        690                 695                 700

Thr Gly Gln Ala Ile Val Pro Glu Ile Met Ile Pro Leu Val Gly Met
705                 710                 715                 720

Lys Thr Glu Leu Glu Val Thr Arg Lys Ala Ala Glu Ala Glu Val Ala
                725                 730                 735

Ala Val Phe Lys Glu Gln Gly Thr Thr Leu Asp Tyr Leu Ile Gly Thr
                740                 745                 750

Met Ile Glu Leu Pro Arg Ala Ala Ile Thr Ala Gly Gln Ile Ala Asp
            755                 760                 765

Val Ala Asp Phe Phe Ser Phe Gly Thr Asn Asp Leu Thr Gln Thr Thr
770                 775                 780

Leu Gly Leu Ser Arg Asp Asp Ala Gly Ser Phe Leu Pro Tyr Tyr Val
785                 790                 795                 800

Asp His Gly Leu Leu Pro Lys Asp Pro Phe Val Ser Ile Asp Arg Glu
                805                 810                 815

Gly Val Gly Ala Leu Val Arg Met Gly Ala Glu Asn Gly Arg Lys Thr
                820                 825                 830

Lys Ser Asn Leu Lys Leu Gly Val Cys Gly Glu His Gly Gly Asp Pro
            835                 840                 845

Asp Ser Ile Ala Phe Phe Glu Ser Val Gly Leu Asp Tyr Val Ser Cys
        850                 855                 860

Ser Pro Phe Arg Val Pro Val Ala Arg Leu Ala Ala Gln Ala Ala
865                 870                 875                 880

Leu Ala Ala Lys Lys Ala Lys Ala Ser Ser
                885                 890

<210> SEQ ID NO 4
<211> LENGTH: 840
<212> TYPE: PRT
<213> ORGANISM: Clostridium symbiosum

<400> SEQUENCE: 4

-continued

```
Met Ala Lys Trp Val Tyr Lys Phe Glu Glu Gly Asn Ala Ser Met Arg
 1               5                  10                  15

Asn Leu Leu Gly Gly Lys Gly Cys Asn Leu Ala Glu Met Thr Ile Leu
                20                  25                  30

Gly Met Pro Ile Pro Gln Gly Phe Thr Val Thr Thr Glu Ala Cys Thr
            35                  40                  45

Glu Tyr Tyr Asn Ser Gly Lys Gln Ile Thr Gln Glu Ile Gln Asp Gln
        50                  55                  60

Ile Phe Glu Ala Ile Thr Trp Leu Glu Glu Leu Asn Gly Lys Lys Phe
65                  70                  75                  80

Gly Asp Thr Glu Asp Pro Leu Leu Val Ser Val Arg Ser Ala Ala Arg
                85                  90                  95

Ala Ser Met Pro Gly Met Met Asp Thr Ile Leu Asn Leu Gly Leu Asn
            100                 105                 110

Asp Val Ala Val Glu Gly Phe Ala Lys Lys Thr Gly Asn Pro Arg Phe
        115                 120                 125

Ala Tyr Asp Ser Tyr Arg Arg Phe Ile Gln Met Tyr Ser Asp Val Val
    130                 135                 140

Met Glu Val Pro Lys Ser His Phe Glu Lys Ile Ile Asp Ala Met Lys
145                 150                 155                 160

Glu Glu Lys Gly Val His Phe Asp Thr Asp Leu Thr Ala Asp Asp Leu
                165                 170                 175

Lys Glu Leu Ala Glu Lys Phe Lys Ala Val Tyr Lys Glu Ala Met Asn
            180                 185                 190

Gly Glu Glu Phe Pro Gln Glu Pro Lys Asp Gln Leu Met Gly Ala Val
        195                 200                 205

Lys Ala Val Phe Arg Ser Trp Asp Asn Pro Arg Ala Ile Val Tyr Arg
    210                 215                 220

Arg Met Asn Asp Ile Pro Gly Asp Trp Gly Thr Ala Val Asn Val Gln
225                 230                 235                 240

Thr Met Val Phe Gly Asn Lys Gly Glu Thr Ser Gly Thr Gly Val Ala
                245                 250                 255

Phe Thr Arg Asn Pro Ser Thr Gly Glu Lys Gly Ile Tyr Gly Glu Tyr
            260                 265                 270

Leu Ile Asn Ala Gln Gly Glu Asp Val Val Ala Gly Val Arg Thr Pro
        275                 280                 285

Gln Pro Ile Thr Gln Leu Glu Asn Asp Met Pro Asp Cys Tyr Lys Gln
    290                 295                 300

Phe Met Asp Leu Ala Met Lys Leu Glu Lys His Phe Arg Asp Met Gln
305                 310                 315                 320

Asp Met Glu Phe Thr Ile Glu Glu Gly Lys Leu Tyr Phe Leu Gln Thr
                325                 330                 335

Arg Asn Gly Lys Arg Thr Ala Pro Ala Ala Leu Gln Ile Ala Cys Asp
            340                 345                 350

Leu Val Asp Glu Gly Met Ile Thr Glu Glu Ala Val Val Arg Ile
        355                 360                 365

Glu Ala Lys Ser Leu Asp Gln Leu Leu His Pro Thr Phe Asn Pro Ala
    370                 375                 380

Ala Leu Lys Ala Gly Glu Val Ile Gly Ser Ala Leu Pro Ala Ser Pro
385                 390                 395                 400

Gly Ala Ala Ala Gly Lys Val Tyr Phe Thr Ala Asp Glu Ala Lys Ala
                405                 410                 415
```

-continued

```
Ala His Glu Lys Gly Glu Arg Val Ile Leu Val Arg Leu Glu Thr Ser
            420                 425                 430

Pro Glu Asp Ile Glu Gly Met His Ala Ala Glu Gly Ile Leu Thr Val
            435                 440                 445

Arg Gly Gly Met Thr Ser His Ala Ala Val Val Ala Arg Gly Met Gly
            450                 455                 460

Thr Cys Cys Val Ser Gly Cys Gly Glu Ile Lys Ile Asn Glu Glu Ala
465                 470                 475                 480

Lys Thr Phe Glu Leu Gly Gly His Thr Phe Ala Glu Gly Asp Tyr Ile
            485                 490                 495

Ser Leu Asp Gly Ser Thr Gly Lys Ile Tyr Lys Gly Asp Ile Glu Thr
            500                 505                 510

Gln Glu Arg Ser Val Ser Gly Ser Phe Glu Arg Ile Met Val Trp Ala
            515                 520                 525

Asp Lys Phe Arg Thr Leu Lys Val Arg Thr Asn Ala Asp Thr Pro Glu
            530                 535                 540

Asp Thr Leu Asn Ala Val Lys Leu Gly Ala Glu Gly Ile Gly Leu Cys
545                 550                 555                 560

Arg Thr Glu His Met Phe Phe Glu Ala Asp Arg Ile Met Lys Ile Arg
            565                 570                 575

Lys Met Ile Leu Ser Asp Ser Val Glu Ala Arg Glu Glu Ala Leu Asn
            580                 585                 590

Glu Leu Ile Pro Phe Gln Lys Gly Asp Phe Lys Ala Met Tyr Lys Ala
            595                 600                 605

Leu Glu Gly Arg Pro Met Thr Val Arg Tyr Leu Asp Pro Pro Leu His
            610                 615                 620

Glu Phe Val Pro His Thr Glu Glu Gln Ala Glu Leu Ala Lys Asn
625                 630                 635                 640

Met Gly Leu Thr Leu Ala Glu Val Lys Ala Lys Val Asp Glu Leu His
            645                 650                 655

Glu Phe Asn Pro Met Met Gly His Arg Gly Cys Arg Leu Ala Val Thr
            660                 665                 670

Tyr Pro Glu Ile Ala Lys Met Gln Thr Arg Ala Val Met Glu Ala Ala
            675                 680                 685

Ile Glu Val Lys Glu Glu Thr Gly Ile Asp Ile Val Pro Glu Ile Met
            690                 695                 700

Ile Pro Leu Val Gly Glu Lys Lys Glu Leu Lys Phe Val Lys Asp Val
705                 710                 715                 720

Val Val Glu Val Ala Glu Gln Val Lys Lys Glu Lys Gly Ser Asp Met
            725                 730                 735

Gln Tyr His Ile Gly Thr Met Ile Glu Ile Pro Arg Ala Ala Leu Thr
            740                 745                 750

Ala Asp Ala Ile Ala Glu Glu Ala Glu Phe Phe Ser Phe Gly Thr Asn
            755                 760                 765

Asp Leu Thr Gln Met Thr Phe Gly Phe Ser Arg Asp Asp Ala Gly Lys
            770                 775                 780

Phe Leu Asp Ser Tyr Tyr Lys Ala Lys Ile Tyr Glu Ser Asp Pro Phe
785                 790                 795                 800

Ala Arg Leu Asp Gln Thr Gly Val Gly Gln Leu Val Glu Met Ala Val
            805                 810                 815

Lys Lys Gly Arg Gln Thr Arg Pro Gly Leu Lys Cys Gly Ile Cys Gly
            820                 825                 830

Glu His Gly Glu Ile Leu Leu Pro
```

<210> SEQ ID NO 5
<211> LENGTH: 2676
<212> TYPE: DNA
<213> ORGANISM: Komagataeibacter xylinus

<400> SEQUENCE: 5

| | | | | | |
|---|---|---|---|---|---|
| tcaggcgggg | ttgccaacct | tgctgcgggt | ggcaagggcg | gcctgagccg | ccgcaaggcg | 60 |
| ggccaccggc | acgcggaagg | gcgagcacga | tacatagtcc | agcccgactt | cctcaaagaa | 120 |
| cgcgatggaa | tccgggtcgc | caccatgctc | gccacagatg | cccagcttga | ggtcggggct | 180 |
| ggtctgccgc | ccccgctcca | cgccaaggcg | cacgagcgcg | cccacgccat | cacggtcgat | 240 |
| ggacacgaac | gggtcgcgcg | gcagcaggcc | gttatcgaca | taataaggca | ggaacgaacc | 300 |
| cgcatcatca | cgcgacaggc | caaaggtggt | ctgggtcagg | tcgttggtgc | cgaacgagaa | 360 |
| gaaatcggca | tattccgcaa | tcctgtccgc | ctggatggcg | gcacgcggca | gttcgatcat | 420 |
| ggtgccaata | taatagttga | ggttggtgcc | ctcttccttc | agcacgcggg | cgatctcgtc | 480 |
| ttcggcagcg | cggcgggtag | tggccagttc | ggcctgcgtt | gccaccagcg | ggatcatgat | 540 |
| ctcggggcgg | atgggcttgc | cgagttcctt | ctccacgatc | acggcggcct | ggatcagcgc | 600 |
| gcgcacctgc | atggcataga | tttccgggct | ggtcaggcca | aggcggcagc | ctcggtggcc | 660 |
| cagcatcggg | ttggtctcgg | ccagcgccgc | gcaccgggca | cgcacctctt | ccacgctctt | 720 |
| gcccagcgcc | tgcgccactt | cgaccatctc | ggcttccgca | tgcggcagga | attcgtgcag | 780 |
| cggcgggtcg | agcaggcgca | cggttaccgg | cagcccggcc | atgatgcgga | acaggctggc | 840 |
| gaagtcatca | cgctggaaag | gcagcagccc | cgcaatggcc | ttctggcgca | ccagttcgtc | 900 |
| atcggcaatg | atcatctggc | gcacgaggcc | gatgcgatca | gggccgaaga | acatgtgctc | 960 |
| cgtgcgggca | aggccaatgc | cttccgcgcc | aaagcgccgg | gcggtggcgg | catcgtcggg | 1020 |
| cgtttcggca | ttggcgcgca | cgccaaggcg | gcgcacgctg | tcggcccagc | ccatgagcgt | 1080 |
| gttgaaatca | tcggacaggg | tgggggctat | ggtgggcacg | cggcccagat | agacagcccc | 1140 |
| cgtgccgcca | tcaagcgtga | tccactcgcc | ctgcgcgatg | gtatgcgtgc | cgatggtcat | 1200 |
| ggtgccggcg | gcgtaatcga | catggatgct | gccagcgcct | gccacgcaca | cgcggcccat | 1260 |
| gccacgcgcc | accacggcgg | cgtgcgaggt | catgccgcca | cgggtggtga | gcacgccacg | 1320 |
| ggcggcatgc | atgccgtgca | cgtcctccgg | cgaggtctcg | atacggacca | ggatcacatc | 1380 |
| ctcgcccttt | gccgcccgtg | cttcacactc | tcagccgag | aacacgaccg | caccggcagc | 1440 |
| agcccctggc | gaggcgggca | ggccgcgcgt | gagctgcacg | cgctcggcct | tggggtcgag | 1500 |
| cgtggggtgc | agaagctggt | caagcgagga | ggcgggcacg | cggcggatcg | catcctcctg | 1560 |
| cgtgatcagg | ccttcacgcg | ccatgtcgat | ggcgatcttg | agtgctgcgg | cagccgtgcg | 1620 |
| cttgccgcta | cgggtctgga | gaatgtgag | gacattgcgc | tggacggtga | attcgatgtc | 1680 |
| ctgcatgtcc | ttgtaatggg | tttcgagcac | cgagcgcaca | cgcatcagct | cggcgtaagc | 1740 |
| ctgcggcagg | gtggtttcca | tcgggtgctg | gcccgcctcg | gcgcgcgcgc | acgccatggg | 1800 |
| ctgcggcgtg | cggatgcccg | ccaccacatc | ctcgccctgc | gcgttgatga | ggtattcgcc | 1860 |
| gtagaagatg | ttctcgcccg | ttgacggatc | acgcgtgaag | catacgccgg | tggcgcagtc | 1920 |
| ctcgcccatg | ttgccgaaca | ccatggactg | cacgttgacc | gccgtgcccc | atgaggccgg | 1980 |
| gatctcgtgc | agcctgcggt | aggtgttggc | gcgcgggttc | atccacgagc | cgaacaccgc | 2040 |
| cccgatcgcg | ccccagagct | ggtcctgcgg | gtcggtgggg | aattcggtgc | cggcatgggt | 2100 |

```
gctgatgagg tggcggtaat cggccacaat ggtgcgccac tgctctgccg tgatggcggt   2160
gtcgtcttcc accttgctgg cgcgcttgaa ctgctcgagc acgtcctcga agtgatggtg   2220
gggcacgccc atcaccaccg agccgtacat ctggatgaag cggcggtagc tgtcccatgc   2280
gaagcgggca tcgccggagg agcgggcaag accttccacc gtctcgtcat tgaggccgag   2340
gttgagcacg gtatccatca tgcccggcat gaacacgcgc gcgcccgagc gcaccgagac   2400
cagcagcggg gccgcggcat cgccaaagcg caggcccatg gattttcaa cccgcgccag    2460 cgcatcggca acctgggcgc gcaggtcatc gggatatttc cggccatttt cataaaaggc   2520
cgaacagact tccgttgtaa tggtgaagcc gggcggcacg gcaggccat tggccgccat     2580 ttccgccagg ttggcgcctt tgccacccag aaggttgcgc atctccgcgc gcccttcgtt   2640
caggccatct ccgaagctat aaacccattt ggtcat                             2676

<210> SEQ ID NO 6
<211> LENGTH: 2523
<212> TYPE: DNA
<213> ORGANISM: Propionibacterium freudenreichii

<400> SEQUENCE: 6
atggcaaaat gggtttataa gttcgaagaa ggcaatgcat ctatgagaaa ccttcttgga     60
ggcaaaggct gcaaccttgc agagatgacc atcttaggaa tgccgattcc acagggcttt   120
actgtaacaa cagaagcttg tacagagtac tacaacagtg gaaaacagat cacacaggaa   180
attcaggatc agattttcga agctatcaca tggttagagg aactgaacgg caagaagttc   240
ggcgacactg aagatccgtt attagtatct gtacgttccg cggcccgcgc atccatgccg   300
ggtatgatgg ataccatcct gaaccttggt ttaaacgacg ttgcagtaga gggctttgca   360
aagaaaacgg gaaatccaag atttgcatat gattcttaca aagatttat ccagatgtat      420 tccgacgtag ttatggaagt tccgaagtcc catttcgaga aaatcatcga tgcgatgaaa   480
gaagaaaagg gcgttcactt cgatacagac ctgactgccg atgatttaaa agagctggct   540
gagaagttca agctgtttta caaagaggct atgaacggcg aagagttccc acaggagccg   600
aaggatcagt taatgggcgc tgttaaagca gttttccgtt cctgggacaa ccctcgtgca   660
atcgtatacc gccgtatgaa cgatatccct ggagactggg gtactgcagt taacgttcag   720
accatggtat ttggtaacaa gggcgagacc agcggtacag cgttgccttc acacgtaac     780 ccatccacag gtgaaaaagg catctacggt gagtacctga tcaatgcaca gggcgaggac   840
gtagttgcag gtgtccgcac accacagcct atcacccagt tagagaacga tatgcctgac   900
tgctacaagc agttcatgga tctggccatg aagctggaga acatttccg tgacatgcag      960 gatatggagt tcacaatcga ggaaggtaaa ttatacttct tacagacacg taacggcaag   1020
agaacagctc cggctgctct tcagattgcc tgcgatttag tagacgaagg catgatcaca   1080
gaggaagagg ctgttgtaag aatcgaagca aaatctcttg atcagttact tcacccgacc   1140
ttcaacccgg ctgctttaaa ggccggcgaa gtaatcggtt ccgctcttcc ggcatctcct   1200
ggcgcagcag caggtaaagt atacttcacc gctgatgagg ctaaggctgc ccacgagaag   1260
ggtgagagag ttatccttgt tcgtcttgag acatctccgg aagatatcga aggtatgcat   1320
gcagccgaag gtatcctgac agtgcgcggc ggtatgacaa gccatgcagc cgtagttgca   1380
cgtggtatgg aacatgctg cgtatccgga tgcggtgaga tcaagatcaa cgaagaagct   1440
aagacattcg aacttggcgg acacacattt gcagagggag attacatctc cttagatggt   1500
```

-continued

| | |
|---|---|
| tccacaggta agatttacaa gggcgacatc gagactcagg aacgttccgt aagcggaagc | 1560 |
| ttcgagcgta tcatggtatg ggctgacaag ttcagaacat taaaggttcg tacaaatgcc | 1620 |
| gacacaccgg aagatacact caatgccgtt aaactgggtg cagagggcat cggtctttgc | 1680 |
| cgtacagagc atatgttctt cgaggctgac agaatcatga agatcagaaa gatgatcctt | 1740 |
| tccgattcag tggaagcaag agaagaggct ctgaacgaat taatcccgtt ccagaagggc | 1800 |
| gatttcaagg ctatgtacaa agctctggaa ggcaggccaa tgacggttcg ctacctggat | 1860 |
| ccgccgctgc atgagttcgt tcctcataca gaagaggagc aggctgaact ggctaagaac | 1920 |
| atgggcctta ctttagcaga agtaaaagca aaagttgacg aattacacga gttcaaccca | 1980 |
| atgatgggcc atcgtggctg ccgtcttgca gttacctatc cggaaattgc aaagatgcag | 2040 |
| acaagagccg ttatggaagc tgctatcgaa gtgaaggaag agacaggaat cgatattgtt | 2100 |
| cctgagatca tgattccgtt agttggcgag aagaaagagc ttaagttcgt taaggacgta | 2160 |
| gttgtggaag tagctgagca ggttaagaaa gagaaaggtt ccgatatgca gtaccacatc | 2220 |
| ggtaccatga tcgaaattcc tcgtgcagct ctcacagcag atgccatcgc tgaggaagca | 2280 |
| gagttcttct ccttcggtac aaacgactta acacagatga cattcggctt ctcccgtgac | 2340 |
| gacgccggca agttcctgga ttcctactat aaagcaaaaa tttatgagtc cgatccattc | 2400 |
| gcaagacttg accagacagg cgttggccag ttagtagaga tggcagttaa gaaaggccgt | 2460 |
| cagacacgtc cgggccttaa gtgcggcatc tgcggcgagc acggcgagat ccttcttccg | 2520 |
| tag | 2523 |

<210> SEQ ID NO 7
<211> LENGTH: 2673
<212> TYPE: DNA
<213> ORGANISM: Acetobacter aceti

<400> SEQUENCE: 7

| | |
|---|---|
| atgacgaaat gggtttacag cttcggtggc ggcctgaacg aaggcagcgc cggaatgcgc | 60 |
| aatctgcttg gtggcaaagg cgccaacctg gcggagatgg cttccatcgg actgccagtg | 120 |
| cctcccggtt ttaccatcac gaccgaagta tgctcggcat actacgataa cggcaatgcc | 180 |
| tacccggctg acctggcaga gcaggtcgcg gcggcccttc atcgcgttga gaaatcggtt | 240 |
| ggtctggtct ttggcgacgc cactgcaccg ctgctggttt cggtccgctc gggcgcccgc | 300 |
| gtctccatgc caggcatgat ggataccgtt ctcaatctcg gtctgaatga cgagacggtt | 360 |
| gaaggtctgg cggcttcctc caaggacgag cggttcgcct gggacagcta tcgccgcttc | 420 |
| atccagatgt atggttccgt cgtgatgggc gtgccgcatc accgtttcga ggatctgctg | 480 |
| gagcaggcca agcacggtct gggcgttaca gacgacacgg ccatcaaggc ttccgactgg | 540 |
| cgcgagatcg tcaaggacta caaggatatc gttcagaaag agaccggcaa gccgttcccg | 600 |
| aacgatccgc aggagcagct ctggggcgcc atcagcgccg tgttcggctc ctggatgaac | 660 |
| ccgcgcgccc acacctaccg caagctgcat gacattcccg caagctgggg caccgccgtc | 720 |
| aacgtgcagg cgatggtctt cggcaacatg ggcgatgact gtgcgaccgg cgtgtgcttc | 780 |
| acccgtgatc cgtctaccgg cgaaaacatc ttctacggcg agtatctggt caacgcgcag | 840 |
| ggcgaagatg tcgtggcggg tatccgcacg ccgcagccca tgtccgccgc ccgtgcggct | 900 |
| gccgatcagt ctccgatgga gaaggtcctg ccggaagcct acaaggaact catgcgtgtg | 960 |
| cgtgacatcc ttgaaaagca ctatcgcgac atgcaggaca tcgagttcac ggtgcagagc | 1020 |
| aacgtgctct acatgctcca gacccggtcc ggtaagcgta cagcagccgc tgctctcaag | 1080 |

```
atcgccatcg acatggcgca ggaaggcctg atcacgcagg aagaagccat ccagcgcgtc    1140
ccacccggct cgctcgacca gcttctgcac ccgacgctcg acccgaaagc cgagaagaac    1200
ctgttctccc gtggcctccc ggcctctccg ggtgccgctg ccggtgcaat cgtctttacg    1260
gctgaagaag tcgaagaccg cgccgccaag ggtgaagatg tcattctggt ccgtatcgaa    1320
acctcaccgg aagacgtgca tggcatgcac gcagcccgtg gcgttctgac gacccgtggt    1380
ggcatgacgt ctcacgccgc cgtcgtggcg cgtggtatgg gtcgtgtctg cgtagctggc    1440
gccggcggta tcaccgtcga ctacaaggcg cagaccatga cggtcggcaa tgtcacgctg    1500
aaaggtggcg actggatcac cctcgatggt ggcacgggcg ctgtctatgt cggcaaggtt    1560
gcgaccattc ccccgactct ctcgggtgac ttcagcacac tgatgggctg gcggatgaa    1620 gtccgtcgcc tgcgcgttcg tgcaaacgcc gagacaccgg aagatgccga cagcccgt     1680 cgcttcggtg ccgaaggcat cggtctgagc cgcacggagc acatgttctt cggtccggac    1740
cgtatcggtt ttgtccgtca gatgatcatg tccgacgatc cggcgacacg caaaaaggcg    1800
attgacgcgc tgctgccgtt ccagcgtgac gatttctcac agatcttccg catcatgagc    1860
ggcctgcctg tgacaatccg tctgctcgat ccgccgctgc atgagttcct ccctcacggc    1920
gagacggaac ttgaggaagt ggccactgcc ctcggtcagt ccgtggagtc cctgcgcgcc    1980
cgtcgctcgg ctctctcgga agccaacccg atgctcggtc accgtggctg tcgtctcggc    2040
atcacctacc ccgagatcta tgcgatgcag gttcgcgcca tcatcgaggc cgctatcgcc    2100
gtctcgaaag agaccggaca ggccatcgtt cctgaaatca tgatcccgct tgtgggcatg    2160
aagacggaac tcgaggtgac ccgcaaggca gcggaagctg aagtcgctgc agtcttcaag    2220
gaacagggca cgacgcttga ttacctcatc ggcaccatga tcgaactgcc gcgcgcagcg    2280
atcacggcag gccagattgc ggacgtggcg gacttcttct cattcggcac caacgatctg    2340
acccagacca cactcggtct gtctcgtgat gatgccggtt cgttcctgcc ctactacgtc    2400
gatcacggcc ttctgccgaa agacccgttc gtctcgatcg accgtgaagg cgtaggggct    2460
ctggtgcgta tgggtgcgga aaatggtcgc aagaccaagt ccaacctgaa gcttggcgtc    2520
tgcggcgaac atggcggcga tccggactcc atcgcgttct cgagagcgt tgggctggat    2580 tacgtttcct gttctccgtt ccgcgtgccg gtggcccgtc ttgccgcagc tcaggctgcc    2640
ttggcggcta aaaaggcaaa agcctcatcc tga                                 2673

<210> SEQ ID NO 8
<211> LENGTH: 2523
<212> TYPE: DNA
<213> ORGANISM: Clostridium symbiosum

<400> SEQUENCE: 8
atggccaagt gggtctacaa gttcgaggag gggaacgcca gcatgcggaa cctgctgggc      60
gggaaggggt gtaacctggc cgaaatgacc atcctgggga tgccgatccc caggggtt      120 accgtcacca cggaagcctg tacggaatac tacaactcgg ggaagcagat cacgcaggag     180
atccaggacc agatcttcga ggccatcacg tggctggagg agctgaacgg caagaagttc     240
ggcgacaccg aggacccgct gctggtcagc gtccgctccg cggcccgcgc ctccatgccg     300
gggatgatgg ataccattct gaatctgggg ctgaacgatg tggccgtcga aggctttgcc     360
aaaaagacgg gcaaccccgg gtttgcctat gacagctacc ggcggtttat ccagatgtac     420
tccgacgtcg tgatggaggt gccgaagtcc cacttcgaga agatcatcga cgcgatgaag     480
```

```
gaggagaagg gcgtgcactt cgacacggac ctgaccgccg acgacctgaa ggagctggcg    540
gagaagttca aggcggtgta caaggaggcg atgaacggcg aggagttccc ccaggagccg    600
aaggaccagc tgatgggcgc ggtgaaggcc gtgttccgct cctgggataa cccgcgcgcc    660
attgtctatc gccgcatgaa tgacatcccc ggcgattggg gcaccgccgt gaacgtgcag    720
acgatggtgt ttgggaacaa gggcgaaacc agcgggacgg gcgtggcctt cacgcgcaac    780
ccctccacgg gcgaaaaagg catttatggg gaatacctga tcaacgccca gggcgaagat    840
gtggtggccg ggtccgcac gccccagccc atcacccagc tggaaaatga tatgcccgat    900
tgctacaaac agttcatgga cctggccatg aagctggaga agcacttccg cgacatgcag    960
gacatggagt tcacgatcga ggaagggaag ctgtacttcc tgcagacgcg caacggcaag   1020 cggacgcgc cggcggccct gcagattgcc tgcgatctgg tcgatgaagg catgatcacg   1080
gaggaggaag cggtggtccg gatcgaagcc aaaagcctgg accagctgct gcatccgacc   1140
ttcaacccgg cggcgctgaa agccggcgaa gtcatcgggt ccgcgctgcc ggccagcccc   1200 ggcgccgcg cggggaaagt ctacttcacc gcggatgaag cgaaagcggc ccatgaaaaa   1260
ggcgaacggg tgatcctggt gcgcctggaa acgagcccgg aagatatcga agggatgcat   1320
gccgccgaag ggatcctgac ggtgcgcggc gggatgacga ccatgccgc cgtcgtggcc   1380 cgcgggatgg gcacgtgctg cgtctccggc tgcggggaaa tcaaaatcaa cgaagaagcg   1440
aaaacgttcg aactgggcgg ccatacgttt gccgaaggcg attatatctc gctggatggg   1500
tcgacgggga aaatttataa aggcgatatc gaaacccagg aacgctcggt cagcggcagc   1560
ttcgaacgca tcatggtctg gcggataaa ttccggacgc tgaaggtgcg caccaatgcc   1620
gatacccggg aagatacct gaatgccgtg aagctgggcg cggaaggcat cgggctgtgc   1680
cgcaccgaac acatgttctt cgaagcggat cggatcatga agatccggaa gatgatcctg   1740
tcggattcgg tggaagcccg ggaagaagcg ctgaatgaac tgatcccgtt ccagaagggc   1800
gatttcaagg cgatgtataa ggcgctggag gccgccccca tgacggtgcg ctatctggac   1860
ccgccgctgc atgaattcgt gccccatacc gaagaagagc aggcggaact ggcgaagaat   1920
atgggcctga ccctggccga agtcaaggcc aaggtggacg aactgcacga attcaatccc   1980
atgatgggcc accgcggctg ccgcctggcg gtgacctatc cggaaatcgc gaagatgcag   2040 acccggccg tgatggaggc ggcgattgag gtgaaggaag agaccggcat cgatatcgtg   2100
cccgagatta tgatcccgct ggtgggcgag aagaaggagc tgaagttcgt gaaggacgtc   2160
gtggtggagg tcgcggagca ggtgaagaag agaaggggt cggacatgca gtatcatatc   2220
gggaccatga ttgagattcc ccgcgcggcg ctgaccgcgg acgccattgc ggaggaggcg   2280
gagttcttct cgttcgggac caatgacctg acccagatga cctttggctt ttcgcgcgac   2340
gacgccggca agtttctgga ctcgtattat aaggcgaaga tttatgagtc ggacccctt   2400 gcgcggctgg atcagaccgg cgtgggccag ctggtcgaga tggcggtgaa gaagggccgc   2460
cagacccgcc cgggcctgaa gtgcggcatt tgcggcgagc atggcgagat tctgctgccg   2520
tga                                                                 2523
```

<210> SEQ ID NO 9
<211> LENGTH: 796
<212> TYPE: PRT
<213> ORGANISM: Gluconacetobacter xylinus

<400> SEQUENCE: 9

Met Asn Ser Leu Met Arg Ser Ala Pro Leu Leu Ala Ala Ala Ile Ala

-continued

```
1               5                   10                  15
Val Cys Ala Leu Thr Gly Leu Tyr Leu Leu Gly Gly Leu Trp Leu
                20                  25                  30

Cys Leu Ile Gly Gly Ser Phe Tyr Tyr Val Ala Gly Val Leu Leu
                35                  40                  45

Leu Val Thr Ala Val Leu Leu Ala Arg Arg Gln Ala Met Ala Leu Thr
50                              55                  60

Val Tyr Ala Val Leu Leu Leu Gly Thr Met Val Trp Ala Val Gln Glu
65                  70                  75                  80

Ala Gly Phe Asp Phe Trp Ala Leu Ala Pro Arg Gly Asp Ile Leu Val
                85                  90                  95

Pro Ile Gly Ile Val Leu Ala Leu Pro Trp Val Thr Arg His Leu Gln
                100                 105                 110

Pro Ala Ser Pro Ala Thr His Leu Pro Leu Phe Gly Ala Ile Gly Ala
                115                 120                 125

Ala Val Val Val Gly Ala Ala Leu Thr Gln Asp Pro Gln Asp Ile
                130                 135                 140

Ala Gly Ser Leu Pro Pro Val Ala Gln Asn Ala Pro Glu Pro Gly Asp
145                 150                 155                 160

Ala His Gln Met Pro Asp Glu Asp Trp Gln Ala Tyr Gly Arg Thr Gln
                165                 170                 175

Phe Gly Asp Arg Phe Ser Pro Leu Lys Gln Val Asn Ala Ser Asn Val
                180                 185                 190

Gly Lys Leu Lys Val Ala Trp Thr Phe Arg Thr Gly Asp Leu Arg Gly
                195                 200                 205

Pro Asn Asp Pro Gly Glu Ile Thr Asp Glu Val Thr Pro Ile Lys Ile
210                 215                 220

Arg Asp Thr Leu Tyr Leu Cys Thr Pro His Gln Ile Leu Phe Ala Leu
225                 230                 235                 240

Asp Ala Lys Thr Gly Gln Gln Arg Trp Lys Phe Asp Pro Lys Leu Ala
                245                 250                 255

Tyr Asn Pro Thr Phe Gln His Leu Thr Cys Arg Gly Val Ser Tyr His
                260                 265                 270

Glu Asp Arg Ala Asp Asp Ala Gln Ala Asp Gly Ala Ala Ala Pro
                275                 280                 285

Ala Glu Cys Ala Arg Arg Ile Phe Leu Pro Thr Asn Asp Gly Gln Leu
                290                 295                 300

Phe Ala Leu Asp Ala Ala Thr Gly Ala Arg Cys Ala Ser Phe Gly Asn
305                 310                 315                 320

Asn Gly Val Val Asn Leu Gln Asp Gly Met Pro Val Lys Thr Leu Gly
                325                 330                 335

Phe Tyr Glu Pro Thr Ser Pro Val Val Thr Asp Thr Thr Val Ile
                340                 345                 350

Val Ser Gly Ala Val Thr Asp Asn Tyr Ser Thr His Glu Pro Ser Gly
                355                 360                 365

Val Thr Arg Gly Phe Asp Val His Thr Gly Ala Leu Lys Trp Ala Phe
                370                 375                 380

Asp Pro Gly Asn Pro Asp Pro Asn Glu Met Pro Ser Glu His His Thr
385                 390                 395                 400

Phe Val Pro Asn Ser Pro Asn Ser Trp Ile Thr Ser Ser Tyr Asp Ala
                405                 410                 415

Lys Leu Asp Leu Ile Tyr Ile Pro Met Gly Val Gln Thr Pro Asp Ile
                420                 425                 430
```

Trp Gly Gly Asn Arg Gly Ala Asp Ala Glu Arg Tyr Ala Ser Ser Ile
            435                 440                 445

Val Ala Leu Asn Ala Thr Thr Gly Arg Leu Val Trp Ser Tyr Gln Thr
450                 455                 460

Val His His Asp Leu Trp Asp Met Asp Ile Pro Ala Gln Pro Ser Leu
465                 470                 475                 480

Val Asp Ile Arg Asn Glu Gln Gly Glu Val Ile Pro Thr Leu Tyr Ala
            485                 490                 495

Pro Ala Lys Thr Gly Asn Ile Phe Val Leu Asp Arg Arg Asn Gly Gln
            500                 505                 510

Pro Val Val Pro Ala Pro Glu His Pro Val Pro Gln Gly Ala Ala Pro
            515                 520                 525

Gly Asp His Val Ser Pro Thr Gln Pro Phe Ser Glu Leu Ser Phe Arg
            530                 535                 540

Pro Lys Lys Leu Leu Thr Asp Ala Asp Met Trp Gly Thr Met Tyr
545                 550                 555                 560

Asp Gln Leu Val Cys Arg Ile Met Phe His Arg Leu Arg Tyr Glu Gly
                565                 570                 575

Thr Phe Thr Pro Pro Ser Leu Gln Gly Thr Leu Val Phe Pro Gly Asn
            580                 585                 590

Leu Gly Met Phe Glu Trp Gly Gly Leu Ala Val Asp Pro Val Arg Gln
            595                 600                 605

Ile Ala Ile Ala Asn Pro Ile Ala Ile Pro Phe Val Ser Lys Leu Ile
            610                 615                 620

Pro Arg Gly Pro Asn Asn Pro Ala Thr Pro Asp Lys Ser Leu Pro Ser
625                 630                 635                 640

Gly Ser Glu Ser Gly Val Gln Pro Gln Phe Gly Val Pro Tyr Gly Val
                645                 650                 655

Asp Leu His Pro Phe Leu Ser Pro Phe Gly Leu Pro Cys Lys Gln Pro
            660                 665                 670

Ala Trp Gly Tyr Met Ser Gly Ile Asp Leu Arg Thr Asn Lys Ile Val
            675                 680                 685

Trp Lys His Arg Asn Gly Thr Ile Arg Asp Ser Ala Pro Leu Pro Leu
            690                 695                 700

Pro Ile Lys Met Gly Val Pro Ser Leu Gly Gly Pro Leu Thr Thr Ala
705                 710                 715                 720

Gly Gly Val Ala Phe Leu Thr Ser Thr Leu Asp Tyr Tyr Ile Arg Ala
                725                 730                 735

Tyr Asp Val Thr Asn Gly Gln Val Leu Trp Gln Asp Arg Leu Pro Ala
            740                 745                 750

Gly Gly Gln Ser Thr Pro Met Thr Tyr Ala Val Asp Gly Lys Gln Tyr
            755                 760                 765

Ile Val Thr Ala Asp Gly Gly His Gly Ser Phe Gly Thr Lys Leu Gly
            770                 775                 780

Asp Tyr Ile Val Ala Tyr Ser Leu Pro Asp Gly Asn
785                 790                 795

<210> SEQ ID NO 10
<211> LENGTH: 2391
<212> TYPE: DNA
<213> ORGANISM: Gluconacetobacter xylinus

<400> SEQUENCE: 10
atgaatagcc tcatgcgctc ggctccccttc ctcgctgcgg ccattgccgt ctgcgccctg    60

```
acgggtctct acctgctggg aggcgggcta tggctgtgtc tcatcggcgg ctccttttat    120
tatgttgtcg ccggtgtgct gctgctggtc acggccgtgc tgctggcgcg gcggcaggcc    180
atggcgctta cggtctatgc cgtgctcctg ctcggcacga tggtgtgggc cgtgcaggaa    240
gccgggtttg atttctgggc gctcgcaccg cggggcgata ttctggtgcc catcggcatc    300
gtgctcgccc tgccgtgggt cacacgtcac ctgcagcctg ccagccccgc cacccacctg    360
cccctgttcg gcgcaattgg cgccgccgtg gtcgtcgttg gcgcggccct gacgcaggac    420
ccgcaggata tcgcgggcag cctgccccca gtcgcgcaga atgcccccga gccgggcgat    480
gcccaccaga tgcctgatga ggactggcag gcctatggcc gcacccagtt cggtgaccgg    540
ttctccccgc tcaagcaggt caatgccagt aatgtcggca aactgaaggt ggcctggacc    600
ttccgcaccg gcgacctgcg cggccccaat gaccccggtg aaatcaccga tgaggtcacc    660
cccatcaaga tccgtgatac gctctatctg tgcacccccc accagatcct gttcgcgctc    720
gatgcgaaga ccgccagca gcggtggaag tttgacccca gctggccta caaccccacc    780
ttccagcacc tgacctgccg tggcgtgtcc tatcatgagg acagggcgga tgacgcgcag    840
gcagccgatg tgccgcagc cccggccgag tgcgcgcgcc gcatcttcct gcccaccaat    900
gatggccagc ttttcgcgct cgatgccgca accggcgcgc gctgcgcaag ctttggcaat    960
aatgcgtgg tgaacctgca ggacggcatg ccggtcaaga cgctgggctt ttatgaaccg   1020
acctcccccc cggtcgtgac cgataccacc gtgatcgtgt ccggcgccgt gaccgacaac   1080
tattccacgc atgagccttc gggggttacg cgcggcttcg acgtgcatac cggcgcgctg   1140
aaatgggcgt tcgaccccgg caatcccgat ccgaacgaga tgccgtccga gcaccacacc   1200
ttcgtgccga actcacccaa ttcgtggatc acgtcgtcct atgatgccaa gctggacctg   1260
atctacatcc ccatgggcgt gcagacgccc gatatctggg gcggcaaccg cggcgccgat   1320
gccgagcgct atgcaagctc catcgtggcg ctgaacgcca ccaccggcag gctggtctgg   1380
tcctaccaga ccgtgcacca cgacctgtgg gacatggaca tccccgccca gcccagcctg   1440
gtcgatatcc gcaacgaaca gggcgaggtc atccccaccc tgtatgcccc ggccaagacc   1500
ggcaacatct tcgtgcttga ccggcgcaac ggccagcccg tggtgcccgc ccccgagcac   1560
ccggtgccgc agggcgcagc ccctggcgat cacgtttcgc ccacgcagcc tttctcggag   1620
ctgagcttcc gccccaagaa gctgctgacc gatgccgata tgtggggcgg cacgatgtat   1680
gaccagctgg tctgccgcat catgttccac cgcctgcgct acgaaggcac attcacgccg   1740
ccttcgctgc agggcacgct ggtcttcccc ggcaatctcg gcatgttcga atggggcggc   1800
cttgcggtcg accccgtgcg ccagatcgcg attgccaacc ccatcgccat tccgttcgtc   1860
tccaaactga tcccgcgcgg cccgaacaac ccggcaacgc ctgacaagtc cctgccctcg   1920
ggctcggaga gtggcgtgca gccgcagttt ggcgtgcctt acggcgtgga cctgcatccg   1980
ttcctctcgc cgtttggcct gccgtgcaag cagcccgcct ggggctacat gtcgggcatc   2040
gacctgcgca ccaacaagat cgtgtggaag caccgcaacg gcacgatccg tgacagcgca   2100
ccgctgcccc tgcccatcaa gatgggcgtg cccagccttg gcggcccgct caccacggcg   2160
ggtggcgtgg ccttcctcac ttccacgctc gattactaca tccgcgccta tgacgtgacg   2220
aacggccagg tgctgtggca ggaccgcctg cctgccggtg gccagtccac gcccatgacc   2280
tatgcggtcg atggcaagca gtacatcgtc acggccgatg gcggcacgg tcgttcggc   2340
accaaactcg gcgactacat cgtcgcctac agcctgcctg acgggaactg a   2391
```

<210> SEQ ID NO 11
<211> LENGTH: 35
<212> TYPE: DNA
<213> ORGANISM: Artificial Sequence
<220> FEATURE:
<223> OTHER INFORMATION: Synthetic primer

<400> SEQUENCE: 11
tagaatactc aagcttggag ctaccagacc gtcca                              35

<210> SEQ ID NO 12
<211> LENGTH: 33
<212> TYPE: DNA
<213> ORGANISM: Artificial Sequence
<220> FEATURE:
<223> OTHER INFORMATION: Synthetic primer

<400> SEQUENCE: 12
tcagaccccg tagaacaaac atgccaaggt tgc                                33

<210> SEQ ID NO 13
<211> LENGTH: 33
<212> TYPE: DNA
<213> ORGANISM: Artificial Sequence
<220> FEATURE:
<223> OTHER INFORMATION: Synthetic primer

<400> SEQUENCE: 13
caacaccttc ttcacttgaa tggggtggcc ttg                                33

<210> SEQ ID NO 14
<211> LENGTH: 35
<212> TYPE: DNA
<213> ORGANISM: Artificial Sequence
<220> FEATURE:
<223> OTHER INFORMATION: Synthetic primer

<400> SEQUENCE: 14
tatagggcga attcgggcag gcggtcctgc cacag                              35

<210> SEQ ID NO 15
<211> LENGTH: 34
<212> TYPE: DNA
<213> ORGANISM: Artificial Sequence
<220> FEATURE:
<223> OTHER INFORMATION: Synthetic primer

<400> SEQUENCE: 15
tcacgccgcc ttcgcgtgaa gaaggtgttg ctga                               34

<210> SEQ ID NO 16
<211> LENGTH: 33
<212> TYPE: DNA
<213> ORGANISM: Artificial Sequence
<220> FEATURE:
<223> OTHER INFORMATION: Synthetic primer

<400> SEQUENCE: 16
aacaccagcg tgcccttcta cggggtctga cgc                                33

<210> SEQ ID NO 17
<211> LENGTH: 36
<212> TYPE: DNA
<213> ORGANISM: Artificial Sequence
<220> FEATURE:
<223> OTHER INFORMATION: Synthetic primer

```
<400> SEQUENCE: 17
cccggggatc ctctaatgac caaatgggtt tatagc                                 36

<210> SEQ ID NO 18
<211> LENGTH: 36
<212> TYPE: DNA
<213> ORGANISM: Artificial Sequence
<220> FEATURE:
<223> OTHER INFORMATION: Synthetic primer

<400> SEQUENCE: 18
agcttgcatg cctgctcagg cggggttgcc aacctt                                 36

<210> SEQ ID NO 19
<211> LENGTH: 36
<212> TYPE: DNA
<213> ORGANISM: Artificial Sequence
<220> FEATURE:
<223> OTHER INFORMATION: Synthetic primer

<400> SEQUENCE: 19
cccggggatc ctctaatggc aaaatgggtt tataag                                 36

<210> SEQ ID NO 20
<211> LENGTH: 36
<212> TYPE: DNA
<213> ORGANISM: Artificial Sequence
<220> FEATURE:
<223> OTHER INFORMATION: Synthetic primer

<400> SEQUENCE: 20
agcttgcatg cctgcctacg gaagaaggat ctcgcc                                 36

<210> SEQ ID NO 21
<211> LENGTH: 36
<212> TYPE: DNA
<213> ORGANISM: Artificial Sequence
<220> FEATURE:
<223> OTHER INFORMATION: Synthetic primer

<400> SEQUENCE: 21
cccggggatc ctctaatgac gaaatgggtt tacagc                                 36

<210> SEQ ID NO 22
<211> LENGTH: 36
<212> TYPE: DNA
<213> ORGANISM: Artificial Sequence
<220> FEATURE:
<223> OTHER INFORMATION: Synthetic primer

<400> SEQUENCE: 22
agcttgcatg cctgctcagg atgaggcttt tgcctt                                 36

<210> SEQ ID NO 23
<211> LENGTH: 36
<212> TYPE: DNA
<213> ORGANISM: Artificial Sequence
<220> FEATURE:
<223> OTHER INFORMATION: Synthetic primer

<400> SEQUENCE: 23
cccggggatc ctctaatggc caagtgggtc tacaag                                 36

<210> SEQ ID NO 24
```

```
<211> LENGTH: 36
<212> TYPE: DNA
<213> ORGANISM: Artificial Sequence
<220> FEATURE:
<223> OTHER INFORMATION: Synthetic primer

<400> SEQUENCE: 24
agcttgcatg cctgctcacg gcagcagaat ctcgcc                            36

<210> SEQ ID NO 25
<211> LENGTH: 3128
<212> TYPE: DNA
<213> ORGANISM: Artificial Sequence
<220> FEATURE:
<223> OTHER INFORMATION: Synthetic pCSa vector

<400> SEQUENCE: 25
gaattcagcc agcaagacag cgatagaggg tagttatcca cgtgaaaccg ctaatgcccc     60
gcaaagcctt gattcacggg gctttccggc ccgctccaaa aactatccac gtgaaatcgc    120
taatcagggt acgtgaaatc gctaatcgga gtacgtgaaa tcgctaataa ggtcacgtga    180
aatcgctaat caaaaaggca cgtgagaacg ctaatagccc tttcagatca acagcttgca    240
aacacccctc gctccggcaa gtagttacag caagtagtat gttcaattag cttttcaatt    300
atgaatatat atatcaatta ttggtcgccc ttggcttgtg acaatgcgc tacgcgcacc     360 ggctccgccc gtgacaacc gcaagcggtt gcccaccgtc gagcgccagc gcctttgccc    420
acaacccggc ggccggccgc aacagatcgt tttataaatt tttttttttg aaaaagaaaa    480
agcccgaaag gcggcaacct ctcgggcttc tggatttccg atcacctgta agtcggacgc    540
gatgcgtccg gcgtagagga tccggagctt atcgactgca cggtgcacca atgcttctgg    600
cgtcaggcag ccatcggaag ctgtggtatg gctgtgcagg tcgtaaatca ctgcataatt    660
cgtgtcgctc aaggcgcact cccgttctgg ataatgtttt tgcgccgac atcataacgg     720 ttctggcaaa tattctgaaa tgagctgttg acaattaatc atcggctcgt ataatgtgtg    780
gaattgtgag cggataacaa tttcacacag gacgagcta ttgattgggt accgagctcg     840
aattcgtacc cggggatcct ctagagtcga cctgcaggca tgcaagcttg ctgttttgg    900 cggatgagag aagattttca gcctgataca gattaaatca gaacgcagaa gcggtctgat    960
aaaacagaat ttgcctggcg gcagtagcgc ggtggtccca cctgacccca tgccgaactc   1020
agaagtgaaa cgccgtagcg ccgatggtag tgtggggtct ccccatgcga gagtagggaa   1080
ctgccaggca tcaaataaaa cgaaaggctc agtcgaaaga ctgggccttt cgttttatct   1140
gttgtttgtc ggtgaacgct ctcctgagta ggacaaatcc gccgggagcg gatttgaacg   1200
ttgcgaagca acggcccgga gggtggcggg caggacgccc gccataaact gccaggcatc   1260
aaattaagca gaaggccatc ctgacggatg cctttttgc cttccgcttc ctcgctcact    1320
gactcgctgc gctcggtcgt tcggctgcgg cgagcggtat cagctcactc aaaggcggta   1380
atacggttat ccacagaatc aggggataac gcaggaaaga acatgtgagc aaaaggccag   1440
caaaaggcca ggaaccgtaa aaaggccgcg ttgctggcgt ttttccatag gctccgcccc   1500
cctgacgagc atcacaaaaa tcgacgctca agtcagaggt ggcgaaaccc gacaggacta   1560
taaagatacc aggcgtttcc ccctggaagc tccctcgtgc gctctcctgt tccgaccctg   1620
ccgcttaccg gatacctgtc cgcctttctc ccttcgggaa gcgtggcgct ttctcatagc   1680
tcacgctgta ggtatctcag ttcggtgtag gtcgttcgct ccaagctggg ctgtgtgcac   1740
gaaccccccg ttcagcccga ccgctgcgcc ttatccggta actatcgtct tgagtccaac   1800
```

```
ccggtaagac acgacttatc gccactggca gcagccactg gtaacaggat tagcagagcg    1860
aggtatgtag gcggtgctac agagttcttg aagtggtggc ctaactacgg ctacactaga    1920
agaacagcat ttggtatctg cgctctgctg aagccagtta ccttcggaaa aagagttggt    1980
agctcttgat ccggcaaaca aaccaccgct ggtagcggtg gtttttttgt ttgcaagcag    2040
cagattacgc gcagaaaaaa aggatctcaa gaagatcctt tgatcttttc tacggggtct    2100
gacgctcagt ggaacgaaaa ctcacgttaa aggctgtgca ggtcgtaaat cactgcataa    2160
ttcgtgtcgc tcaaggcgca ctcccgttct ggataatgtt ttttgcgccg acatcataac    2220
ggttctggca aatattctga aatgagctgt tgacaattaa tcatcggctc gtataatgtg    2280
tggaattgtg agcggataac aatttcacac aggaaacata gatctcccgg gtaccgagct    2340
ctctagaaag aaggagggac gagctattga tggagaaaaa aatcactgga tataccaccg    2400
ttgatatatc ccaatggcat cgtaaagaac attttgaggc atttcagtca gttgctcaat    2460
gtacctataa ccagaccgtt cagctggata ttacggcctt tttaaagacc gtaaagaaaa    2520
ataagcacaa gttttatccg gcctttattc acattcttgc ccgcctgatg aatgctcatc    2580
cggaattccg tatggcaatg aaagacggtg agctggtgat atgggatagt gttcacccct    2640
gttacaccgt tttccatgag caaactgaaa cgttttcatc gctctggagt gaataccacg    2700
acgatttccg gcagtttcta cacatatatt cgcaagatgt ggcgtgttac ggtgaaaacc    2760
tggcctattt ccctaaaggg tttattgaga atatgttttt cgtctcagcc aatccctggg    2820
tgagtttcac cagttttgat ttaaacgtgg ccaatatgga caacttcttc gcccccgttt    2880
tcaccatggg caaatattat acgcaaggcg acaaggtgct gatgccgctg gcgattcagg    2940
ttcatcatgc cgtttgtgat ggcttccatg tcggcagaat gcttaatgaa ttacaacagt    3000
actgcgatga gtggcagggc ggggcgtaat ttttttaagg cagttttta aggcagttat    3060 tggtgccctt aaacgcctgg ttgctacgcc tgaataagtg ataataagcg gatgaatggc    3120
agaaattc                                                            3128
```